United States Patent
Iacono et al.

(10) Patent No.: US 10,941,101 B2
(45) Date of Patent: *Mar. 9, 2021

(54) FORMATION OF ALPHA,BETA-UNSATURATED CARBOXYLIC ACIDS AND SALTS THEREOF FROM METALALACTONES AND ANIONIC POLYELECTROLYTES

(71) Applicant: Chevron Phillips Chemical Company LP, The Woodlands, TX (US)

(72) Inventors: Pasquale Iacono, Bartlesville, OK (US); Mark L. Hlavinka, Tulsa, OK (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/519,674

(22) Filed: Jul. 23, 2019

(65) Prior Publication Data
US 2019/0345089 A1 Nov. 14, 2019

Related U.S. Application Data

(63) Continuation of application No. 16/183,275, filed on Nov. 7, 2018, now Pat. No. 10,392,336, which is a continuation of application No. 15/377,563, filed on Dec. 13, 2016, now Pat. No. 10,160,711.

(60) Provisional application No. 62/267,601, filed on Dec. 15, 2015.

(51) Int. Cl.
*C07C 51/15* (2006.01)
(52) U.S. Cl.
CPC .................... *C07C 51/15* (2013.01)
(58) Field of Classification Search
CPC .................................................. C07C 51/15
See application file for complete search history.

(56) References Cited

U.S. PATENT DOCUMENTS

| | | | |
|---|---|---|---|
| 3,390,128 A | 6/1968 | Hughes et al. | |
| 4,060,480 A | 11/1977 | Reed et al. | |
| 4,452,910 A | 6/1984 | Hopkins et al. | |
| 4,792,620 A * | 12/1988 | Paulik | B01J 31/0231 560/232 |
| 5,376,611 A | 12/1994 | Shveima | |
| 6,107,230 A | 8/2000 | McDaniel et al. | |
| 6,165,929 A | 12/2000 | McDaniel et al. | |
| 6,294,494 B1 | 9/2001 | McDaniel et al. | |
| 6,300,271 B1 | 10/2001 | McDaniel et al. | |
| 6,316,553 B1 | 11/2001 | McDaniel et al. | |
| 6,355,594 B1 | 3/2002 | McDaniel et al. | |
| 6,376,415 B1 | 4/2002 | McDaniel et al. | |
| 6,388,017 B1 | 5/2002 | McDaniel et al. | |
| 6,391,816 B1 | 5/2002 | McDaniel et al. | |
| 6,395,666 B1 | 5/2002 | McDaniel et al. | |
| 6,524,987 B1 | 2/2003 | Collins et al. | |
| 6,548,441 B1 | 4/2003 | McDaniel et al. | |
| 6,548,442 B1 | 4/2003 | McDaniel et al. | |
| 6,576,583 B1 | 6/2003 | McDaniel et al. | |
| 6,613,712 B1 | 9/2003 | McDaniel et al. | |
| 6,632,894 B1 | 10/2003 | McDaniel et al. | |
| 6,667,274 B1 | 12/2003 | Hawley et al. | |
| 6,750,302 B1 | 6/2004 | McDaniel et al. | |
| 6,831,141 B2 | 12/2004 | McDaniel et al. | |
| 6,936,667 B2 | 8/2005 | Jensen et al. | |
| 6,992,032 B2 | 1/2006 | McDaniel et al. | |
| 7,026,494 B1 | 4/2006 | Yang et al. | |
| 7,041,617 B2 | 5/2006 | Jensen et al. | |
| 7,148,298 B2 | 12/2006 | Jensen et al. | |
| 7,199,073 B2 | 4/2007 | Martin et al. | |
| 7,226,886 B2 | 6/2007 | Jayaratne et al. | |
| 7,250,510 B2 | 7/2007 | Organ et al. | |
| 7,294,599 B2 | 11/2007 | Jensen et al. | |
| 7,312,283 B2 | 12/2007 | Martin et al. | |
| 7,470,758 B2 | 12/2008 | Jensen et al. | |
| 7,501,372 B2 | 3/2009 | Thorn et al. | |
| 7,517,939 B2 | 4/2009 | Yang et al. | |
| 7,576,163 B2 | 8/2009 | Yang et al. | |
| 7,601,665 B2 | 10/2009 | McDaniel et al. | |
| 7,619,047 B2 | 11/2009 | Yang et al. | |
| 7,629,284 B2 | 12/2009 | Jensen et al. | |
| 7,884,163 B2 | 2/2011 | McDaniel et al. | |
| 8,309,485 B2 | 11/2012 | Yang et al. | |
| 8,592,632 B2 | 11/2013 | Dahmen et al. | |
| 8,623,973 B1 | 1/2014 | McDaniel et al. | |
| 8,642,803 B2 | 2/2014 | Limbach et al. | |
| 8,697,909 B2 | 4/2014 | Limbach et al. | |
| 8,703,886 B1 | 4/2014 | Yang et al. | |
| 8,940,940 B2 | 1/2015 | Dehn et al. | |
| 9,023,959 B2 | 5/2015 | McDaniel et al. | |

(Continued)

FOREIGN PATENT DOCUMENTS

| CA | 2791834 | 9/2011 |
|---|---|---|
| CN | 103785469 | 5/2014 |

(Continued)

OTHER PUBLICATIONS

Norskov et al, Nature Chemistry, Towards the Computational Design of Solid Catalysts, 2009, 1, pp. 37-46. (Year: 2009).*

(Continued)

*Primary Examiner* — Paul A Zucker
(74) *Attorney, Agent, or Firm* — Eversheds Sutherlands (US) LLP

(57) ABSTRACT

This disclosure provides routes of synthesis of acrylic acid and other α,β-unsaturated carboxylic acids and their salts, including catalytic methods. In an aspect, there is provided a process for producing an α,β-unsaturated carboxylic acid or a salt thereof, the process comprising: (1) contacting in any order a group 8-11 transition metal precursor compound comprising at least one first ligand, at least one second ligand, an olefin, carbon dioxide, a diluent, and an anionic polyaromatic resin with associated metal cations to provide a reaction mixture; and (2) applying conditions to the reaction mixture suitable to produce the α,β-unsaturated carboxylic acid or a salt thereof. Methods of regenerating the polyaromatic resin with associated metal cations are described.

33 Claims, 1 Drawing Sheet

(56) References Cited

U.S. PATENT DOCUMENTS

| | | | |
|---|---|---|---|
| 9,416,087 B2 | 8/2016 | Hlavinka et al. | |
| 9,725,393 B2 | 8/2017 | Hlavinka et al. | |
| 9,783,478 B2 | 10/2017 | Hlavinka et al. | |
| 9,896,405 B2 | 2/2018 | Hlavinka et al. | |
| 10,011,551 B2 | 7/2018 | Limbach et al. | |
| 10,138,196 B2 | 11/2018 | Schaub et al. | |
| 10,155,711 B2 | 12/2018 | Hlavinka et al. | |
| 10,155,712 B2 | 12/2018 | Hlavinka et al. | |
| 10,160,711 B2 * | 12/2018 | Iacono | C07C 51/15 |
| 10,392,336 B2 * | 8/2019 | Iacono | C07C 51/15 |
| 10,550,061 B2 * | 2/2020 | Iacono | B01J 31/10 |
| 2010/0076167 A1 | 3/2010 | McDaniel et al. | |
| 2011/0218359 A1 | 9/2011 | Limbach et al. | |
| 2013/0172616 A1 | 7/2013 | Limbach et al. | |
| 2015/0343431 A1 | 12/2015 | Parvulescu et al. | |
| 2015/0344394 A1 | 12/2015 | Parvulescu et al. | |
| 2016/0102039 A1 | 4/2016 | Hlavinka et al. | |
| 2016/0130208 A1 | 5/2016 | Schäffner et al. | |
| 2016/0229782 A1 | 8/2016 | Hlavinka et al. | |
| 2016/0311745 A1 | 10/2016 | Hlavinka et al. | |
| 2017/0166506 A1 | 6/2017 | Iacono et al. | |
| 2017/0283356 A1 | 10/2017 | Hlavinka et al. | |
| 2017/0349523 A1 | 12/2017 | Hlavinka et al. | |
| 2018/0127346 A1 | 5/2018 | Hlavinka et al. | |
| 2018/0362434 A1 | 12/2018 | Iacono et al. | |
| 2018/0362435 A1 | 12/2018 | Iacono et al. | |
| 2018/0362436 A1 | 12/2018 | Hlavinka et al. | |
| 2019/0062250 A1 | 2/2019 | Hlavinka et al. | |
| 2019/0071381 A1 | 3/2019 | Iacono et al. | |

FOREIGN PATENT DOCUMENTS

| | | | |
|---|---|---|---|
| CN | 103785470 | 5/2014 | |
| CN | 104418719 | 3/2015 | |
| CN | 104418736 | 3/2015 | |
| CN | 104418737 | 3/2015 | |
| CN | 105622383 | 6/2016 | |
| CN | 105622400 | 6/2016 | |
| DE | 112014001125 | 11/2015 | |
| EP | 2797869 | 8/2018 | |
| EP | 3142992 | 9/2018 | |
| IN | 201207472 | 12/2013 | |
| IN | 201404656 | 9/2015 | |
| WO | 2011/107559 | 9/2011 | |
| WO | 2013/098772 | 7/2013 | |
| WO | 2013/186238 | 12/2013 | |
| WO | 2014/003195 | 1/2014 | |
| WO | 2014/130410 | 8/2014 | |
| WO | 2014/198469 | 12/2014 | |
| WO | 2015/018793 | 2/2015 | |
| WO | 2015/132031 | 9/2015 | |
| WO | 2015/173276 | 11/2015 | |
| WO | 2015/173277 | 11/2015 | |
| WO | 2015/173295 | 11/2015 | |
| WO | 2015/173296 | 11/2015 | |
| WO | 2015/173307 | 11/2015 | |
| WO | WO 2015/173296 A1 * | 11/2015 | |
| WO | 2015/197699 | 12/2015 | |
| WO | 2016/057449 | 4/2016 | |
| WO | 2017/106176 | 6/2017 | |
| WO | 2017/178282 | 10/2017 | |

OTHER PUBLICATIONS

International Search Report and the Written Opinion of the International Searching Authority in PCT/US2017/025837 dated Jul. 17, 2017, 9 pages.

International Search Report and Written Opinion for PCT/US2016/066360, dated Jul. 27, 2017, 8 pages.

International Search Report and Written Opinion of the Searching Authority, PCT/US2015/054128, dated Dec. 21, 2015, 11 pages.

Al-Ghamdi, et al., "Activity Relationship to Screen Ni-Bisphosphine Complexes for the Oxidative Coupling of CO2 and Ethylene," Organometallics, 2017, vol. 36, pp. 1107-1112.

Brand, et al., "Acid-Base Characterization of Aluminum Oxide Surfaces with XPS" J. Phys. Chem. B. 2004, 108, p. 6017-6024.

Bruckmeier et al., "Formation of Methyl Acrylate from CO2 and Ethylene via Methylation of Nickelalactones", Organometallics, 2010, vol. 29, pp. 2199-2202.

Deutschmann, "Heterogeneous Catalysis and Solid Catalysts, 2. Development and Types of Solid Catalysts," Ullmann's Encyclopedia of Industrial Chemistry, published online Oct. 15, 2011, pp. 483-549, doi: 10.1002/14356007.o05_o02.

Eigenberger, "Catalytic Fixed-Bed Reactors," Ullmann's Encyclopedia of Industrial Chemistry, 2012, pp. 1-66, doi:10.1002/14356007.b04_199.pub2.

Fischer et al., "Zur Synthese und Charakterisierung van N, N'—Tetramethylethylendiamin-nickelacyclopropionat", Z. anorg. allg. Chem., 1989, vol. 577, pp. 111-114.

Fischer, et al.., "A key step in the formation of acrylic acid from CO2 and ethylene: the transformation of a Nickelalactone into a nickel-acrylate complex"; Chem. Commun., 2006, pp. 2510-2512.

Gordillo et al. "Catalytic route to acrylates from alkenes and CO2" Abstracts of Papers, 245th ACS National Meeting & Exposition, New Orleans, LA, United States, Apr. 7-11, 2013 (2013), INOR-1109. Language: English, Database: CAPLUS.

Hendricksen, "Catalytic Formation of Acrylate from Carbon Dioxide and Ethene," Chemistry, a European Journal, 2014, vol. 20, pp. 12037-12040.

Hoberg et al., "Nickel(O)—Induzierte C—C-Verkniipfung Zwischen Kohlendioxid und Ethylen Sowie Mono-Oder Di-Substituierten Alkenen"; Journal of Organometallic Chemistry, 1983, vol. 251, pp. C51-C53.

Huguet et al., "Nickel—Catalyzed Direct Carboxylation of Olefins with CO2: One-Pot Synthesis of a, β-Unsaturated Carboxylic Acid Salts", Chem. Eur. J., 2014, vol. 20, pp. 16858-16862.

Jin et al., "Effect of Sodium Cation on Metallacycle β-Hydride Elimination in CO2-Ethylene Coupling to Acrylates", Chem. Eur. J., 2014, vol. 20, pp. 3205-3211.

Jin et al., "Lewis Acid Induced β-Elimination from a Nickelalactone: Efforts toward Acrylate Production from CO2 and Ethylene", Organometallics, 2013, vol. 32, pp. 2152-2159.

Knopf et al., "A family of cis-macrocyclic diphosphines: modular, stereoselective synthesis and application in Catalytic CO2/ethylene coupling", Chemical Science, 2017, vol. 8 (Issue 2), pp. 1463-1468. doi:10.1039/c6sc03614g.

Kraus, "Ni-Catalyzed Synthesis of Acrylic Acid Derivatives from CO2 and Ethylene," Topics in Organometallic Chemistry, vol. 53, 2015, p. 199-223.

Krillov et al., "Carboxylic acid derivatives via catalytic carboxylation of unsaturated hydrocarbons: whether the nature of a reductant may determine the mechanism of CO2 incorporation?", Dalton Trans., 2015, vol. 44, 16212-16223.

Langer et al., "A new set of nickelacyclic carboxylates ("nickelalactones") containing pyridine as supporting ligand: synthesis, structures and application in C—C- and C—S linkage reactions"; Journal of Organometallic Chemistry, 2004, vol. 689, pp. 2952-2962.

Lejkowski et al, "The First Catalytic Synthesis of an Acrylate from CO2 and an Alkene—A Rational Approach"; Chem. Eur. J., 2012, vol. 18, pp.

Limbach et al., "Investigation of fundamental steps in the formation of acrylates from CO2 and ethylene", Abstracts of Papers, 243rd ACS National Meeting & Exposition, San Diego, CA, United States, Mar. 25-29, 2012 (2012), NOR-1216. Language: English, Database: CAPLUS.

Limbach, "Acrylates from Alkenes and CO2, the Stuff That Dreams Are Made of," Advances in Organometallic Chemistry 2015, vol. 63, Chapter 4, pp. 175-202.

Limbach, et al., "CO2 as C1 building block for the synthesis of acrylates and beyond", From Abstracts of Papers, 247th ACS National Meeting & Exposition, Dallas, TX, United States, Mar. 16-20, 2014 (2014), CATL-116. Language: English, Database: CAPLUS.

(56) References Cited

OTHER PUBLICATIONS

Manzini et al., "Enhanced activity and recyclability of palladium complexes in the catalytic synthesis of sodium acrylate from CO2 and ethylene" ChemCatChem, 2016. doi:10.1002/cctc.201601150.

Manzini et al., "Palladium- and Nickel-Catalyzed Synthesis of Sodium Acrylate from Ethylene, CO2, and Phenolate Bases: Optimization of the Catalytic System for a Potential Process", Eur. J. Org. Chem., 2015, pp. 7122-7130.

Manzini et al., "Synthesis of acrylates from olefins and CO2 using sodium alkoxides as bases", Catalysis Today, 2016, http://dx.doi.org/10.1016/j.cattod.2016.03.025.

Newkirk, "Drying and Decomposition of Sodium Carbonate," Analytical Chemistry, vol. 30, No. 5, 1958, pp. 982-984.

Norskov et al., Nature Chemistry, Towards the Computational Design of Solid Catalysts, 2009, 1, pp. 37-46.

Papai et al., "Mechanistic Details of Nickel(O)—Assisted Oxidative Coupling of CO2 with C2H4"; Organometallics, 25004, vol. 23, pp. 5252-5259.

Pinnavaia, T. J., "Intercalated Clay Catalysts," Science, 1983, vol. 220, No. 4595, pp. 365-371.

Plessow et al., "Acrylate Formation from CO2 and Ethylene Mediated by Nickel Complexes: A Theoretical Study", Oganometallics, 2014, vol. 33, pp. 3657-3668.

Plessow et al., "Mechanistic Details of the Nickel-Mediated Formation of Acrylates from CO2, Ethylene and Methyllodide", Organometallics, 2013, vol. 32, pp. 3327-3338.

Prasetyo, "Development of heterogenized catalyst systems for the synthesis of acrylic acid derivatives from carbon dioxide and ethylene," University of Stuttgart, Doctoral Thesis, Date of oral test: Apr. 20, 2015, 275 pages.

Stieber et al., "Acrylate formation from CO2 and ethylene: catalysis with palladium and mechanistic insight", Chem. Commun., 2015, vol. 51, pp. 10907-10909.

Thomas, J.M., "Sheet Silicate Intercalates: New Agents for Unusual Chemical Conversions*", Intercalation Chemistry, Academic Press, Inc., 1982, Ch. 3, pp. 55-99.

Wang, "Synthesis of Acrylic Acid Derivatives from CO2 and Ethylene," Chem, 3, 211-228, 2017.

Yu et al., "Carboxylation of olefins/alkynes with CO2 to industrially relevant acrylic acid derivatives", Journal of CO2 Utilization, 2013, vol. 1, pp. 60-68.

\* cited by examiner

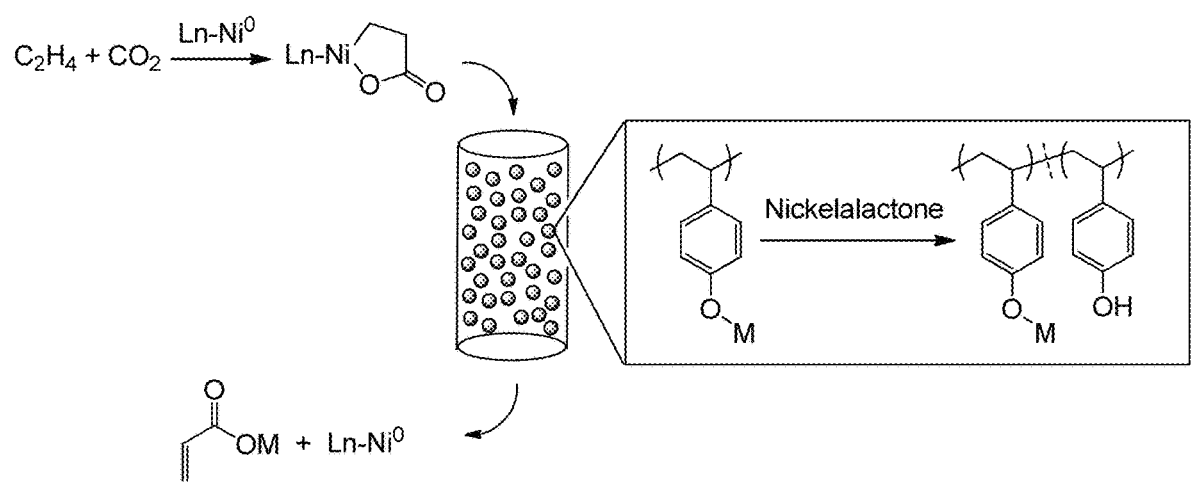

FORMATION OF ALPHA,BETA-UNSATURATED CARBOXYLIC ACIDS AND SALTS THEREOF FROM METALALACTONES AND ANIONIC POLYELECTROLYTES

CROSS REFERENCE TO RELATED APPLICATIONS

This application is a continuation of U.S. patent application Ser. No. 16/183,275, now U.S. Pat. No. 10,392,336, filed Nov. 7, 2018, which is a continuation of U.S. patent application Ser. No. 15/377,563, filed Dec. 13, 2016, now U.S. Pat. No. 10,160,711, which claims the benefit of U.S. Provisional Patent Application No. 62/267,601, filed Dec. 15, 2015, each of which is incorporated herein by reference in its entirety.

TECHNICAL FIELD OF THE INVENTION

This disclosure relates to routes of synthesis of acrylic acid and other α,β-unsaturated carboxylic acids, including catalytic methods.

BACKGROUND

The majority of industrially synthesized chemical compounds are prepared from a limited set of precursors, whose ultimate sources are primarily fossil fuels. As these reserves diminish, it would be beneficial to use a renewable resource, such as carbon dioxide, which is a non-toxic, abundant, and economical $C_1$ synthetic unit. The coupling of carbon dioxide with other unsaturated molecules holds tremendous promise for the direct preparation of molecules currently prepared by traditional methods not involving $CO_2$.

One could envision the direct preparation of acrylates and carboxylic acids through this method, when carbon dioxide is coupled with olefins. Currently, acrylic acid is produced by a two-stage oxidation of propylene. The production of acrylic acid directly from carbon dioxide and ethylene would represent a significant improvement due to the greater availability of ethylene and carbon dioxide versus propylene, the use of a renewable material ($CO_2$) in the synthesis, and the replacement of the two-step oxygenation process currently being practiced.

Therefore, what is needed are improved methods for preparing acrylic acid and other α,β-unsaturated carboxylic acids, including catalytic methods.

SUMMARY OF THE INVENTION

This summary is provided to introduce various concepts in a simplified form that are further described below in the detailed description. This summary is not intended to identify required or essential features of the claimed subject matter nor is the summary intended to limit the scope of the claimed subject matter.

In an aspect, this disclosure provides processes, including catalytic processes, for producing α,β-unsaturated carboxylic acids or salts thereof utilizing a soluble or an insoluble anionic polyelectrolyte system. When the anionic polyelectrolyte system is insoluble or the reaction system is otherwise heterogeneous, these processes represent an improvement over homogeneous processes that result in poor yields and involve challenging separation/isolation procedures. Therefore, conventional methods generally make isolation of the desired α,β-unsaturated carboxylic acid (e.g., acrylic acid) difficult. In contrast, the processes disclosed herein utilize an anionic polyelectrolyte having associated metal cations that generally provides a heterogeneous reaction mixture. When combined with a catalyst such as a nickel catalyst, ethylene and carbon dioxide can be coupled to form a metalalactone, and the anionic polyelectrolyte can subsequently destabilize the metalalactone which eliminates a metal acrylate. By developing the disclosed heterogeneous system, there is now provided a distinct advantage in ease of separation of the desired product from the catalytic system. Moreover, the anionic polyelectrolytes can result in surprisingly high yields of the desired α,β-unsaturated carboxylic acid, such as acrylic acid.

According to an aspect, one such process for producing an α,β-unsaturated carboxylic acid, or a salt thereof, can comprise:

(1) contacting
  (a) a metalalactone comprising at least one ligand;
  (b) a diluent; and
  (c) an anionic polyelectrolyte having associated metal cations to provide a reaction mixture; and
(2) applying conditions to the reaction mixture suitable to induce a metalalactone elimination reaction to produce the α,β-unsaturated carboxylic acid or a salt thereof.

In a further aspect, there is provided another such process for the formation of an α,β-unsaturated carboxylic acid, or a salt thereof, and this process can comprise:

(1) contacting
  (a) a metalalactone comprising at least one ligand;
  (b) a diluent; and
  (c) an anionic polyelectrolyte having associated metal cations to provide a reaction mixture comprising an adduct of the metalalactone and the anionic polyelectrolyte and its associated metal cations; and
(2) applying conditions to the reaction mixture suitable to form the α,β-unsaturated carboxylic acid or a salt thereof.

According to additional aspects of this disclosure, there is provided a process for producing an α,β-unsaturated carboxylic acid or a salt thereof, in which this process can comprise:

(1) contacting in any order
  (a) a transition metal precursor compound comprising at least one first ligand;
  (b) optionally, at least one second ligand;
  (c) an olefin;
  (d) carbon dioxide ($CO_2$);
  (e) a diluent; and
  (f) an insoluble anionic polyelectrolyte having associated metal cations to provide a reaction mixture; and
(2) applying conditions to the reaction mixture suitable to form the α,β-unsaturated carboxylic acid or a salt thereof.

This summary and the following detailed description provide examples and are explanatory only of the invention. Accordingly, the foregoing summary and the following detailed description should not be considered to be restrictive. Additional features or variations thereof can be provided in addition to those set forth herein, such as for example, various feature combinations and sub-combinations of these described in the detailed description.

BRIEF DESCRIPTION OF THE DRAWING

The FIGURE illustrates an embodiment or aspect of this disclosure, showing the use an anionic polyelectrolyte stationary phase in a column configuration, in which formation of the acrylate coupling reaction of ethylene and $CO_2$ to form a metalalactone such as a nickelalactone in a mobile phase can be effected, and the resulting nickelalactone destabilized by the polyelectrolyte stationary phase to form an acrylate product.

DETAILED DESCRIPTION OF THE INVENTION

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

While compositions and methods are described in terms of "comprising" various components or steps, the compositions and methods can also "consist essentially of" or "consist of" the various components or steps, unless stated otherwise.

The terms "a," "an," and "the" are intended to include plural alternatives, e.g., at least one. For instance, the disclosure of "an anionic polyelectrolyte," "a diluent," "a catalyst," and the like, is meant to encompass one, or mixtures or combinations of more than one, anionic polyelectrolyte, diluent, catalyst, and the like, unless otherwise specified.

The term "hydrocarbon" refers to a compound containing only carbon and hydrogen. Other identifiers can be utilized to indicate the presence of particular groups in the hydrocarbon, for instance, a halogenated hydrocarbon indicates the presence of one or more halogen atoms replacing an equivalent number of hydrogen atoms in the hydrocarbon.

As used herein, the term "α,β-unsaturated carboxylic acid" and its derivatives refer to a carboxylic acid having a carbon atom of a carbon-carbon double bond attached to the carbonyl carbon atom (the carbon atom bearing the double bonded oxygen atom). Optionally, the α,β-unsaturated carboxylic acid can contain other functional groups, heteroatoms, or combinations therof.

The term "polyelectrolyte" is used herein to mean a polymeric (macromolecular) substance which comprises a multiply-charged polyion, together with an equivalent amount of counter ions. Therefore, an "anionic polyelectrolyte" refers to a polyelectrolyte that comprises a multiply-charged polyanion, together with an equivalent amount of cations. The charge on the polyion typically resides on heteroatoms such as oxygen, nitrogen or sulfur, or on groups such as sulfonate. The structural part of the polyelectrolyte that bears the charged moieties can be pendant groups off a polymer backbone or can be part of the polymeric backbone itself. The term "polyelectrolyte" is used to refer to both soluble species and insoluble species, such as some of the poly(vinylphenol)-based materials and the phenol-formaldehyde based materials described herein. The multiply-charged polyanion may also be referred to as a base, and the associated metal ion as simply a counter ion, metal ion, or Lewis acid as appropriate.

Although the terms "polyphenol" and "polyaromatic" are used herein to describe anionic polyelectrolytes in which a phenoxide moiety carries the negative charge in the polyelectrolyte, and although these terms may be used interchangeably as the context allows, these terms are generally used herein to describe specific types of anionic polyelectrolyte polymers that are somewhat different, as set out here.

[1] The terms "polyphenol" and "polyphenoxide" are generally used herein to describe a specific type of anionic polyelectrolyte polymer, for example, the polymeric materials such as poly(4-vinylphenol) and metallated poly(4-vinylphenoxide) that typically include a pendant phenol, phenoxide, or substituted analogs thereof that are bonded to a polymeric backbone. Therefore, the oxygen of the phenoxide group bears the negative charge.

[2] The term "polyaromatic" is also generally used herein to describe a specific type of anionic polyelectrolyte resin or polymer, for example, the phenol-formadehyde crosslinked resins and their analogs, in which the phenol aromatic group and methylene moieties are part of an extended crosslinked network. Therefore, aromatic groups in the "polyaromatic" structure are hydroxylated, hydroxymetallated, or otherwise functionalized with a group that carries the negative charge in the anionic polyelectrolyte (e.g. thiolate, alkyl amide). Crosslinked networks that are prepared using various phenol or polyhydroxyarene co-monomers also included in this definition. The term "phenolic resin" may be used to describe these materials as well.

A "polyhydroxyarene" is used herein to a phenol-type monomer that includes more than one hydroxyl group. Resorcinol (also termed, benzenediol or m-dihydroxybenzene) is a typical polyhydroxyarene.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Various numerical ranges are disclosed herein. When Applicants disclose or claim a range of any type, Applicants' intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicants disclose, in an aspect of the invention, that one or more steps in the processes disclosed herein can be conducted at a temperature in a range from 10° C. to 75° C. This range should be interpreted as encompassing temperatures in a range from "about" 10° C. to "about" 75° C.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants can be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants can be unaware of at the time of the filing of the application.

The term "substituted" when used to describe a group, for example, when referring to a substituted analog of a particular group, is intended to describe the compound or group wherein any non-hydrogen moiety formally replaces hydrogen in that group or compound, and is intended to be non-limiting. A compound or group can also be referred to herein as "unsubstituted" or by equivalent terms such as "non-substituted," which refers to the original group or compound. "Substituted" is intended to be non-limiting and include inorganic substituents or organic substituents as specified and as understood by one of ordinary skill in the art.

The terms "contact product," "contacting," and the like, are used herein to describe compositions and methods wherein the components are contacted together in any order, in any manner, and for any length of time, unless specified otherwise. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, "contacting" two or more components can result in a reaction product or a reaction mixture. Consequently, depending upon the circumstances, a "contact product" can be a mixture, a reaction mixture, or a reaction product.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

The present disclosure is directed generally to methods for forming α,β-unsaturated carboxylic acids, or salts thereof. An illustrative example of a suitable α,β-unsaturated carboxylic acid is acrylic acid.

According to one aspect, this disclosure provides for the formation of an α,β-unsaturated carboxylic acids and salts thereof from metalalactones and anionic polyelectrolytes. One example of the α,β-unsaturated carboxylic acid salt formation from exemplary metalalactones and anionic polyelectrolytes is illustrated in Scheme 1, which provides for a nickel catalytic coupling reaction between an olefin and $CO_2$ and formation of an acrylate. As explained herein, Scheme 1 is not limiting but is exemplary, and each reactant, catalyst, polymer, and product are provided for illustrative purposes.

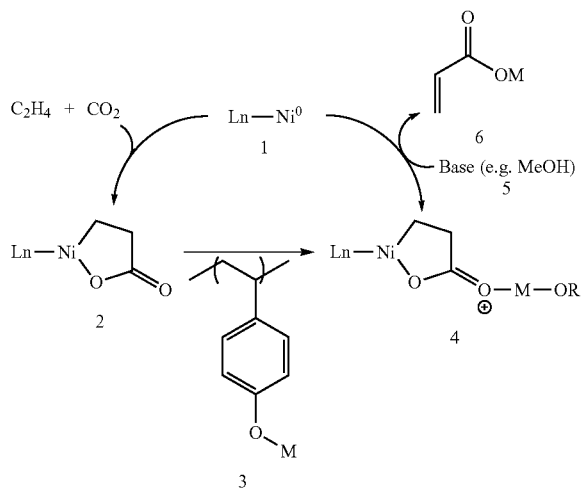

Scheme 1

In Scheme 1, a transition metal catalyst as disclosed herein is illustrated generally by a nickel(0) catalyst at compound 1, and the olefin disclosed herein, generally an α-olefin, is illustrated generally by ethylene. In the presence of the catalyst 1, the olefin couples with $CO_2$ to form the metalalactone 2. Metalalactone 2 is destabilized by its interaction with an anionic polyelectrolyte, an example of which is shown in Scheme 1 as a metal poly(4-vinylphenoxide) 3. While not intending to be bound by theory, metal poly(4-vinylphenoxide) 3 is thought to interact with metalalactone 2 in some way, for example to form an adduct of some type, such as one illustrated as adduct 4. Reaction with the combined metal poly(4-vinylphenoxide) 3 and metalalactone 2 (or adduct of some type, represented generally as 4) with a base 5 both eliminates or releases the metal acrylate 6 from adduct 4 and regenerates catalyst compound 1 and byproduct neutral polymer (here, poly(4-vinylphenol), which is regenerated to the anionic polyelectrolyte reactant, for example metal poly(4-vinylphenoxide) 3, upon its reaction with the base 5. In other words, elimination of the metal acrylate from 4 occurs to regenerate catalyst compound 1 and byproduct neutral polymer (here, poly(4-vinylphenol)), which is regenerated to the anionic polyelectrolyte reactant 3 upon its reaction with a base 5. In the presence of additional ethylene and $CO_2$, catalyst 1 is converted to metalalactone 2.

One exemplary base illustrated in Scheme 1 is a hydroxide base, but a carbonate base, similar inorganic bases, and a wide range of other bases can be used, particularly metal-containing bases. Metal containing bases can include any basic inorganic metal compound or mixture of compounds that contain metal cations or cation sources, for example, alkali and alkaline earth metal compounds such as oxides, hydroxides, alkoxides, aryloxides, amides, alkyl amides, arylamides, and carbonates like calcium hydroxide. In an aspect, the reaction of Scheme 1 can be conducted using certain bases as disclosed, but if desired, other organic bases such as some alkoxide, aryloxide, amide, alkyl amide, arylamide bases, or the like can be excluded. Typically, the inorganic bases such as alkali metal hydroxides have been found to work well.

Generally, the anionic polyelectrolyte and associated cations used in the processes disclosed herein can comprise (or consist essentially of, or consist of) an insoluble anionic polyelectrolyte, a soluble anionic polyelectrolyte, or a combination thereof. That is, the anionic polyelectrolyte material can be soluble, insoluble, or only partially or slightly soluble in the diluent or reaction mixture. It is further contemplated that mixtures or combinations of two or more anionic polyelectrolytes can be employed in certain aspects of the disclosure. Therefore, the "anionic polyelectrolyte" is a polymeric material which comprises a multiply-charged polyanion, together with an equivalent amount of counter cations, and is used generally to refer to both soluble materials and insoluble materials.

In an aspect, the anionic polyelectrolyte (and associated cations) can be used in the absence of an alkoxide or aryloxide base. Further, the reactions and processes disclosed herein can be conducted in the absence of an alkoxide, an aryloxide, an alkylamide, an arylamide, and/or substituted analogs thereof. That is, additional bases with their associated counter ions are not required to effect the processes disclosed herein.

According to an aspect, the anionic polyelectrolyte and associated cations used in the processes can be used in the absence of a solid support. That is the anionic polyelectrolyte can be used is its natural polymeric form without being bonded to or supported on any insoluble support, such as an inorganic oxide or mixed oxide material.

In an aspect, the term anionic polyelectrolyte is used to refer to and include such polyelectrolytes that comprise alkoxide, aryloxide, acrylate, (meth)acrylate, sulfonate, alkyl thiolate, aryl thiolate, alkyl amide, or aryl amine groups, along with associated metal cations, such as any alkali metal cation, alkaline earth cation, or metal cations having varying Lewis acidities. While aspects of this disclosure are exemplified with anionic polyelectrolytes having aryloxide (or "phenoxide") anionic groups, these are to be considered exemplary of any of the anionic polyelectrolytes provided herein. Therefore, terms such as poly(vinyl aryloxide), poly(vinyl phenoxide), poly(hydroxystyrene), and the like are generally used interchangeably unless the context provides otherwise.

Accordingly, the term anionic polyelectrolyte is used generally to include such anionic polyelectrolytes as a poly(vinyl arylaxide), a poly(vinyl alkoxide), a poly(acrylate), a poly((meth)acrylate)), a poly(styrene sulfonate), a phenol-formaldehyde resin, a polyhydroxyarene-formaldehyde resin (such as a resorcinol-formaldehyde resin), a polyhydroxyarene- and fluorophenol-formaldehyde resin (such as a resorcinol- and 2-fluorophenol-formaldehyde resin), a poly(vinyl arylamide), a poly(vinyl alkylamide), or combinations thereof, along with associated metal cations. Polymers that generally fall under the phenol-formadehyde type of crosslinked resins may be referred to as polyaromatic resins. Co-polymers of these specific types of anionic polyelectrolytes are also included in this disclosure. The polyelectrolyte core structure can be substituted on the polymer backbone or the pendant groups that also contain the typical oxygen, nitrogen, or sulfur heteroatoms, and such substituted variations are included in this disclosure and use of the term anionic polyelectrolyte. For example, any of the anionic polyelectrolytes can be substituted with electron-withdrawing groups or electron-donating groups or even combinations thereof.

Anionic polyelectrolytes such as those used herein include associated cations, particularly associated metal cations, including Lewis acidic metal cations and cations with low Lewis acidity. According to an aspect, the associated metal cations can be an alkali metal, an alkaline earth metal, or any combination thereof. Typical associated metal cations can be, can comprise, or can be selected from lithium, sodium, potassium, magnesium, calcium, strontium, barium, aluminum, or zinc, and the like. Generally, sodium or potassium associated metal cations have been found to work well. Therefore, cations with a range of Lewis acidities in the particular solvent can be useful according to this disclosure.

One aspect of the disclosed process provides for using an anionic polyelectrolyte that comprises, consists essentially of, or consists of sodium(polyvinylphenoxide), including sodium(poly-4-vinylphenoxide). Other salts, such as the potassium salt, of the poly-4-vinylphenoxide are also useful.

In a further aspect, useful anionic polyelectrolytes can include phenol-formaldehyde resins, which are cross-linked materials derived from the condensation reaction of phenol with formaldehyde, that are treated with a base or a metal cation source. Advantages of using treated phenol-formaldehyde resins include their insolubility, which allows the use of a range of solvents with these materials, and their relatively high phenol concentration that can be functionalized using a metal base such as an alkali metal hydroxide. An early version of the thermosetting phenol formaldehyde resins formed from the condensation reaction of phenol with formaldehyde is Bakelite™, and various phenol-formaldehyde resins used herein may be referred to generically as "bakelite" resins. In the context of this disclosure, the use of terms such as bakelite or general terms such as phenol-formaldehyde resins contemplates that these materials will be treated with a metal-containing base or a metal cation source such as sodium hydroxide prior to their use in the processes disclosed.

In addition, other useful anionic polyelectrolytes include substituted phenol-formaldehyde resins that are also generally crosslinked into insoluble resins. These resins can be formed from the condensation reaction of one or more of phenol, a polyhydroxyarene such as resorcinol (also, benzenediol or m-dihydroxybenzene), and/or their substituted analogs with formaldehyde. Therefore, these materials include resins made with more than one phenol as co-monomer. Treatment with bases such as NaOH or KOH also provides a ready method of functionalizing the polyaromatic polymers for the reactivity described herein.

In one example, a resin can be prepared using the monomer combination of resorcinol (m-dihydroxybenzene) and fluorophenol monomers with formaldehyde, and sodium-treated to generate the anionic polyelectrolyte. While not intending to be theory bound, the meta-dihydroxybenzene is believed to add additional ion chelation functionality to the resin. Subsequent base (e.g. sodium hydroxide) treatment can be used to generate the anionic polyelectrolyte.

Finally, this aspect is not intended to be limiting. Therefore, other suitable anionic polyelectrolytes that can be used include a number of anionic polyelectrolytes which include carboxylic acid/carboxylate groups. Examples include but are not limited to polyacrylic acid, polymethacrylic acid, poly(D,L-glutamic) acid, polyuronic acid (alginic, galacturonic, glucuronic, and the like), glycosaminoglycans (hyaluronic acid dermatan sulphate, chondroitin sulphate, heparin, heparan sulphate, and keratan sulphate), poly(D,L-aspartic acid), poly(styrene sulfonate), poly(phosphate), polynucleic acids, and so forth.

In those aspects and embodiments in which polymer support variations are used and/or in which the polyelectrolyte itself is a solid that is insoluble in the diluent of the reaction, such solid state polyelectrolyte embodiments can have any suitable surface area, pore volume, and particle size, as would be recognized by those of skill in the art. For instance, the solid polyelectrolyte can have a pore volume in a range from 0.1 to 2.5 mL/g, or alternatively, from 0.5 to 2.5 mL/g. In a further aspect, the solid polyelectrolyte can have a pore volume from 1 to 2.5 mL/g. Alternatively the pore volume can be from 0.1 to 1.0 mL/g. Additionally, or alternatively, the solid polyelectrolyte can have a BET surface area in a range from 10 to 750 m$^2$/g; alternatively, from 100 to 750 m$^2$/g; or alternatively, from 100 to 500 m$^2$/g or alternatively from 30 to 200 m$^2$/g. In a further aspect, the solid polyelectrolyte can have a surface area of from 100 to 400 m$^2$/g, from 200 to 450 m$^2$/g, or from 150 to 350 m$^2$/g. The average particle size of the solid polyelectrolyte can vary greatly depending upon the process specifics, however, average particle sizes in the range of from 5 to 500 μm, from 10 to 250 μm, or from 25 to 200 μm, are often employed. Alternatively ⅛ inch (3.2 mm) to ¼ inch (6.4 mm) pellets or beads can also be used.

The present disclosure also provides for various modifications of the polymeric anionic stationary phase (anionic polyelectrolytes), for example, in a column or other suitable solid state configuration. Further various modifications of the polymeric anionic stationary phase (anionic polyelectrolytes), for example, in a column or other suitable solid state configuration are useful in the processes disclosed herein. For example, acid-base reactions that generate the anionic polyelectrolyte from the neutral polymer can be effected using a wide range of metal bases, including alkali and alkaline hydroxides, alkoxides, aryloxides, amides, alkyl or aryl amides, and the like, such that an assortment of electrophiles can be used in nickelalactone destabilization as demonstrated herein for the polyvinylphenols.

Polymer modifications can also include using variants of the poly(vinylphenol), that can be prepared by polymerization of protected hydroxyl-substituted styrenes (such as acetoxystyrene) having a variety of organic and inorganic substituents, such as alkyls, halogens, and heteroatom substituents, typically followed by hydrolysis. Such adjustments can provide flexibility for tailoring the reaction according to the specific olefin to be coupled with $CO_2$, the reaction rate, the catalytic turnover, as well as additional reaction parameters and combinations of reaction parameters.

In a further aspect, polymer modifications can also include using co-polymers based on, for example, the co-polymerization of a protected hydroxyl-substituted styrene with other monomers (e.g., styrenes and/or (meth)acrylates) to produce libraries of polymeric electrophiles. Such a library can be utilized to test and match the specific anionic polyelectrolyte with the specific olefin, to improve or optimize reaction rate, catalytic turnover, reaction selectivity, and the like. Further polymer support variations can also be used, for example, polymers can be supported onto beads or other surfaces. Alternatively, one class of polymer support variation that is possible for use with this technology is the cast polymer that can function as an ion exchange membrane. Alternatively, the anionic polyelectrolyte can be unsupported and used in the absence of any support.

The disclosed processes can further include the step of reacting adduct 4 of the metalalactone 2 and anionic polyelectrolyte 3 with a base 5, also termed a regenerative base. The regenerative base 5 can comprise a metal ion or a metal ion source. In the example of Scheme 1, the anionic polyelectrolyte can be a metal poly(4-vinylphenoxide), which is formed upon the reaction of the neutral polymer, for example poly(4-vinylphenol), with a base 5 such as a metal-containing base. For example, the metal in a metal-containing base can be, but is not limited to, a metal of Groups 1, 2, 12 or 13, such as lithium, sodium, potassium, rubidium, cesium, magnesium, calcium, zinc, aluminum or gallium. As illustrated in Scheme 1, the reaction of a base 5 with the combination of the anionic polyelectrolyte 3 and metalalactone 2 (or adduct of some type, represented generally as 4) with a metal-containing base 5 both eliminates or releases the metal acrylate 6 from 4 and regenerates catalyst compound 1 and byproduct neutral polymer (e.g. poly(4-vinylphenol) in Scheme 1), which is regenerated to the anionic polyelectrolyte reactant upon its reaction with a regenerative base 5. Various bases 5 can be used according to this disclosure.

The step of regenerating the anionic polyelectrolyte can be effected by contacting the anionic polyelectrolyte with a regenerative base 5 comprising a metal cation following the formation of the α,β-unsaturated carboxylic acid or a salt thereof. A wide range of bases 5 can be used for this regeneration step. For example, the regenerative base 5 can be or can comprise metal-containing bases which can include any reactive inorganic basic metal compound or mixture of compounds that contain metal cations or cation sources, for example, alkali and alkaline earth metal compounds such as oxides, hydroxides, alkoxides, aryloxides, amides, alkyl amides, arylamides, and carbonates. Suitable bases include or comprise, for example, carbonates (e.g., $Na_2CO_3$, $Cs_2CO_3$, $MgCO_3$), hydroxides (e.g., $Mg(OH)_2$, $Ca(OH)_2$, NaOH, KOH), alkoxides (e.g., $Al(O^iPr)_3$, $Na(O^tBu)$, $Mg(OEt)_2$), aryloxides (e.g. $Na(OC_6H_5)$, sodium phenoxide) and the like. Typically, this regeneration step further comprising or is followed by the step of washing the anionic polyelectrolyte with a solvent or the diluent.

According to an aspect, the regenerative base 5 can be or can comprise a nucleophilic base, for example a metal hydroxide or metal alkoxide. While the regenerative base 5 can comprise a non-nucleophilic base, the processes disclosed herein work in the absence of a non-nucleophilic base such an alkali metal hydride or an alkaline earth metal hydride, an alkali metal or alkaline earth metal dialkylamides and diarylamides, an alkali metal or alkaline earth metal hexalkyldisilazane, and an alkali metal or alkaline earth metal dialkylphosphides and diarylphosphides.

Typically, the inorganic bases such as alkali metal hydroxides or alkali metal alkoxides have been found to work the best. However, in one aspect, the reaction of Scheme 1 can be conducted using some bases but in the absence of certain other organic bases such as an alkoxide, aryloxide, amide, alkyl amide, arylamide, or the like. In another aspect, the anionic polyelectrolyte (and associated cations) can be used and regenerated in the absence of an alkoxide or aryloxide. Further, the reactions and processes disclosed herein can be conducted in the absence of an alkoxide, an aryloxide, an alkylamide, an arylamide, an amine, a hydride, a phosphazene, and/or substituted analogs thereof. For example, the processes disclosed herein can be conducted in the absence of sodium hydride, an aryloxide salt (such as a sodium aryloxide), an alkoxide salt (such as a sodium tert-butoxide), and/or a phosphazene.

The processes disclosed herein typically are conducted in the presence of a diluent. Mixtures and combinations of diluents can be utilized in these processes. The diluent can comprise, consist essentially of, or consist of, any suitable solvent or any solvent disclosed herein, unless otherwise specified. For example, the diluent can comprise, consist essentially of, or consist of a non-protic solvent, a protic solvent, a non-coordinating solvent, or a coordinating solvent. For instance, in accordance with one aspect of this disclosure, the diluent can comprise a non-protic solvent.

Representative and non-limiting examples of non-protic solvents can include tetrahydrofuran (THF), 2,5-Me$_2$THF, acetone, toluene, chlorobenzene, pyridine, carbon dioxide, olefin and the like, as well as combinations thereof. In accordance with another aspect, the diluent can comprise a weakly coordinating or non-coordinating solvent. Representative and non-limiting examples of weakly coordinating or non-coordinating solvents can include toluene, chlorobenzene, paraffins, halogenated paraffins, and the like, as well as combinations thereof.

In accordance with yet another aspect, the diluent can comprise a carbonyl-containing solvent, for instance, ketones, esters, amides, and the like, as well as combinations thereof. Representative and non-limiting examples of carbonyl-containing solvents can include acetone, ethyl methyl ketone, ethyl acetate, propyl acetate, butyl acetate, isobutyl isobutyrate, methyl lactate, ethyl lactate, N,N-dimethylformamide, and the like, as well as combinations thereof. In still another aspect, the diluent can comprise THF, 2,5-Me$_2$THF, methanol, acetone, toluene, chlorobenzene, pyridine, anisole, or a combination thereof; alternatively, THF; alternatively, 2,5-Me$_2$THF; alternatively, methanol; alternatively, acetone; alternatively, toluene; alternatively, chlorobenzene; or alternatively, pyridine.

In an aspect, the diluent can comprise (or consist essentially of, or consist of) an aromatic hydrocarbon solvent. Non-limiting examples of suitable aromatic hydrocarbon solvents that can be utilized singly or in any combination include benzene, toluene, xylene (inclusive of ortho-xylene, meta-xylene, para-xylene, or mixtures thereof), and ethylbenzene, or combinations thereof; alternatively, benzene; alternatively, toluene; alternatively, xylene; or alternatively, ethylbenzene.

In an aspect, the diluent can comprise (or consist essentially of, or consist of) a halogenated aromatic hydrocarbon solvent. Non-limiting examples of suitable halogenated aromatic hydrocarbon solvents that can be utilized singly or in any combination include chlorobenzene, dichlorobenzene, and combinations thereof; alternatively, chlorobenzene; or alternatively, dichlorobenzene.

In an aspect, the diluent can comprise (or consist essentially of, or consist of) an ether solvent. Non-limiting examples of suitable ether solvents that can be utilized singly or in any combination include dimethyl ether, diethyl ether, diisopropyl ether, di-n-propyl ether, di-n-butyl ether, diphenyl ether, methyl ethyl ether, methyl t-butyl ether, dihydrofuran, tetrahydrofuran (THF), 2,5-Me$_2$THF, 1,2-dimethoxyethane, 1,4-dioxane, anisole, and combinations thereof; alternatively, diethyl ether, dibutyl ether, THF, 2,5-Me$_2$THF, 1,2-dimethoxyethane, 1,4-dioxane, and combinations thereof; alternatively, THF; or alternatively, diethyl ether.

In a further aspect, any of these aforementioned diluents can be excluded from the diluent or diluent mixture. For example, the diluent can be absent a phenol or a substituted phenol, an alcohol or a substituted alcohol, an amine or a substituted amine, water, an ether, an aliphatic hydrocarbon solvent, an aromatic hydrocarbon solvent, an aldehyde or ketone, an ester or amide, and/or absent a halogenated aromatic hydrocarbon, or any substituted analogs of these diluents halogenated analogs, including any of the aforementioned diluents. Therefore, Applicant reserves the right to exclude any of the diluents provided herein.

In all aspects and embodiments disclosed herein, the diluent can include or comprise carbon dioxide, olefin, or combinations thereof. At least a portion of the diluent can comprise the α,β-unsaturated carboxylic acid or the salt thereof, formed in the process.

In this disclosure, the term transition metal precursor, transition metal compound, transition metal catalyst, transition metal precursor compound, carboxylation catalyst, transition metal precursor complex and similar terms refer to a chemical compound that serves as the precursor to the metalalactone, prior to the coupling of the olefin and carbon dioxide at the metal center of the transition metal precursor compound. Therefore, the metal of the transition metal precursor compound and the metal of the metalalactone are the same. In some aspects, some of the ligands of the transition metal precursor compound carry over and are retained by the metalalactone following the coupling reaction. In other aspects, the transition metal precursor compound loses its existing ligands, referred to herein as first ligands, in presence of additional ligands such as chelating ligands, referred to herein as second ligands, as the metalalactone is formed. Therefore, the metalalactone generally incorporates the second (added) ligand(s), though in some aspects, the metalalactone can comprise the first ligand(s) that were bound in the transition metal precursor compound.

According to an aspect, the transition metal catalyst or compound used in the processes can be used without being immobilized on a solid support. That is the transition metal catalyst can be used is its usual form which is soluble in most useful solvents, without being bonded to or supported on any insoluble support, such as an inorganic oxide or mixed oxide material.

A prototypical example of a transition metal precursor compound that loses its initial ligands in the coupling reaction in the presence of a second (added) ligand, wherein the metalalactone incorporates the second (added) ligand(s), is contacting Ni(COD)$_2$ (COD is 1,5-cyclooctadiene) with a diphosphine ligand such as 1,2-bis(dicyclohexylphosphino)ethane in a diluent in the presence of ethylene and CO$_2$ to form a nickelalactone with a coordinated 1,2-bis(dicyclohexylphosphino)ethane bidentate ligand.

Accordingly, in an aspect, the process for producing an α,β-unsaturated carboxylic acid or a salt thereof, can comprise:
(1) contacting in any order
  (a) a transition metal precursor compound comprising at least one first ligand;
  (b) optionally, at least one second ligand;
  (c) an olefin;
  (d) carbon dioxide (CO$_2$);
  (e) a diluent; and
  (f) an anionic polyelectrolyte having associated metal cations to provide a reaction mixture; and
(2) applying conditions to the reaction mixture suitable to form the α,β-unsaturated carboxylic acid or a salt thereof.

Generally, the processes disclosed herein employ a metalalactone or a transition metal precursor compound or complex. The transition metal of the metalalactone, or of the transition metal precursor compound, can be a Group 3 to Group 8 transition metal or, alternatively, a Group 8 to Group 11 transition metal. In one aspect, for instance, the transition metal can be Fe, Co, Ni, Cu, Ru, Rh, Pd, Ag, Ir, Pt, or Au, while in another aspect, the transition metal can be Fe, Ni, or Rh. Alternatively, the transition metal can be Fe; alternatively, the transition metal can be Co; alternatively, the transition metal can be Ni; alternatively, the transition metal can be Cu; alternatively, the transition metal can be Ru; alternatively, the transition metal can be Rh; alternatively, the transition metal can be Pd; alternatively, the transition metal can be Ag; alternatively, the transition metal can be Ir; alternatively, the transition metal can be Pt; or alternatively, the transition metal can be Au.

In particular aspects contemplated herein, the transition metal can be Ni. Hence, the metalalactone can be a nickelalactone and the transition metal precursor compound can be a Ni-ligand complex in these aspects.

The ligand of the metalalactone and/or of the transition metal precursor compound, can be any suitable neutral electron donor group and/or Lewis base. For instance, the suitable neutral ligands can include sigma-donor solvents that contain a coordinating atom (or atoms) that can coordinate to the transition metal of the metalalactone (or of the transition metal precursor compound). Examples of suitable coordinating atoms in the ligands can include, but are not limited to, O, N, S, and P, or combinations of these atoms. In some aspects consistent with this disclosure, the ligand can be a bidentate ligand.

In an aspect, the ligand used to form the metalalactone and/or the transition metal precursor compound can be an ether, an organic carbonyl, a thioether, an amine, a nitrile, or a phosphine. In another aspect, the ligand used to form the metalalactone or the transition metal precursor compound can be an acyclic ether, a cyclic ether, an acyclic organic carbonyl, a cyclic organic carbonyl, an acyclic thioether, a cyclic thioether, a nitrile, an acyclic amine, a cyclic amine, an acyclic phosphine, or a cyclic phosphine.

Suitable ethers can include, but are not limited to, dimethyl ether, diethyl ether, dipropyl ether, dibutyl ether, methyl ethyl ether, methyl propyl ether, methyl butyl ether, diphenyl ether, ditolyl ether, tetrahydrofuran, 2-methyltetrahydrofuran, 2,5-dimethyltetrahydrofuran, 2,3-dihydrofuran, 2,5-dihydrofuran, furan, benzofuran, isobenzofuran, dibenzofuran, tetrahydropyran, 3,4-dihydro-2H-pyran, 3,6-dihydro-2H-pyran, 2H-pyran, 4H-pyran, 1,3-dioxane, 1,4-dioxane, morpholine, and the like, including substituted derivatives thereof.

Suitable organic carbonyls can include ketones, aldehydes, esters, and amides, either alone or in combination, and illustrative examples can include, but are not limited to, acetone, acetophonone, benzophenone, N,N-dimethylformamide, N,N-dimethylacetamide, methyl acetate, ethyl acetate, and the like, including substituted derivatives thereof.

Suitable thioethers can include, but are not limited to, dimethyl thioether, diethyl thioether, dipropyl thioether, dibutyl thioether, methyl ethyl thioether, methyl propyl thioether, methyl butyl thioether, diphenyl thioether, ditolyl thioether, thiophene, benzothiophene, tetrahydrothiophene, thiane, and the like, including substituted derivatives thereof.

Suitable nitriles can include, but are not limited to, acetonitrile, propionitrile, butyronitrile, benzonitrile, 4-methylbenzonitrile, and the like, including substituted derivatives thereof.

Suitable amines can include, but are not limited to, methyl amine, ethyl amine, propyl amine, butyl amine, dimethyl amine, diethyl amine, dipropyl amine, dibutyl amine, trimethyl amine, triethyl amine, tripropyl amine, tributyl amine, aniline, diphenylamine, triphenylamine, tolylamine, xylylamine, ditolylamine, pyridine, quinoline, pyrrole, indole, 2-methylpyridine, 3-methylpyridine, 4-methylpyridine, 2,5-dimethylpyrrole, 2,5-diethylpyrrole, 2,5-dipropylpyrrole, 2,5-dibutylpyrrole, 2,4-dimethylpyrrole, 2,4-diethylpyrrole, 2,4-dipropylpyrrole, 2,4-dibutylpyrrole, 3,4-dimethylpyrrole, 3,4-diethylpyrrole, 3,4-dipropylpyrrole, 3,4-dibutylpyrrole, 2-methylpyrrole, 2-ethylpyrrole, 2-propylpyrrole, 2-butylpyrrole, 3-methylpyrrole, 3-ethylpyrrole, 3-propylpyrrole, 3-butylpyrrole, 3-ethyl-2,4-dimethylpyrrole, 2,3,4,5-tetramethylpyrrole, 2,3,4,5-tetraethylpyrrole, 2,2'-bipyridine, 1,8-Diazabicyclo[5.4.0]undec-7-ene, di(2-pyridyl)dimethylsilane, N,N,N',N'-tetramethylethylenediamine, 1,10-phenanthroline, 2,9-dimethyl-1,10-phenanthroline, glyoxal-bis(mesityl)-1,2-diimine and the like, including substituted derivatives thereof. Suitable amines can be primary amines, secondary amines, or tertiary amines.

Suitable phosphines and other phosphorus compounds can include, but are not limited to, trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, tricyclohexylphosphine, trimethyl phosphite, triethyl phosphite, tripropyl phosphite, triisopropyl phosphite, tributyl phosphite and tricyclohexyl phosphite, 2-(di-t-butylphosphino)biphenyl, 2-di-t-butylphosphino-1,1'-binaphthyl, 2-(di-t-butylphosphino)-3,6-dimethoxy-2',4',6'-tri-i-propyl-1,1'-biphenyl, 2-di-t-butylphosphino-2'-methylbiphenyl, 2-(di-t-butylphosphinomethyl)pyridine, 2-di-t-butylphosphino-2',4',6'-tri-i-propyl-1,1'-biphenyl, 2-(dicyclohexylphosphino) biphenyl, (S)-(+)-(3,5-dioxa-4-phospha-cyclohepta[2,1-a;3,4-a']dinaphthalen-4-yl)dimethylamine, 2-(diphenylphosphino)-2'-methoxy-1,1'-binaphthyl, 1,2,3,4,5-pentaphenyl-1'-(di-t-butylphosphino)ferrocene, 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)-ethane, 1,2-bis(diisopropylphosphino)ethane, 1,2-bis(dibutyl-phosphino)ethane, 1,2-bis(di-t-butyl-phosphino)ethane, 1,2-bis(dicyclohexylphosphino)ethane, 1,3-bis(dicyclohexylphosphino)propane, 1,3-bis(diisopropylphosphino)propane, 1,3-bis(diphenylphosphino)propane, 1,3-bis(di-t-butylphosphino) propane, 1,4-bis(diisopropylphosphino)butane, 1,4-bis(diphenylphosphino)butane, 2,2'-bis[bis(3,5-dimethylphenyl)phosphino]-4,4',6,6'-tetramethoxybiphenyl, 2,6-bis(di-t-butylphosphinomethyl)pyridine, 2,2'-bis(dicyclohexylphosphino)-1,1'-biphenyl, bis(2-dicyclohexylphosphinophenyl)ether, 5,5'-bis(diphenylphosphino)-4,4'-bi-1,3-benzodioxole, 2-t-butylphosphinomethylpyridine, bis (diphenylphosphino)ferrocene, bis(diphenylphosphino) methane, bis(dicyclohexylphosphino)methane, bis(di-t-butylphosphino)methane, and the like, including substituted derivatives thereof.

In other aspects, the ligand used to form the metalalactone or the transition metal precursor compound can be a carbene, for example, a N-heterocyclic carbene (NHC) compound. Representative and non-limiting examples of suitable N-heterocyclic carbene (NHC) materials include the following:

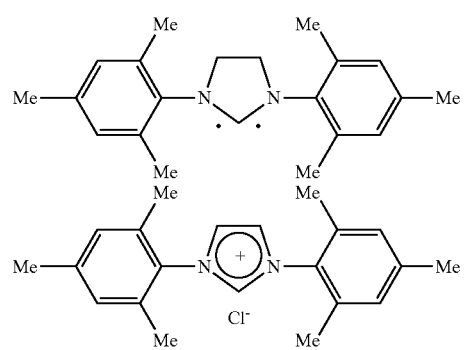

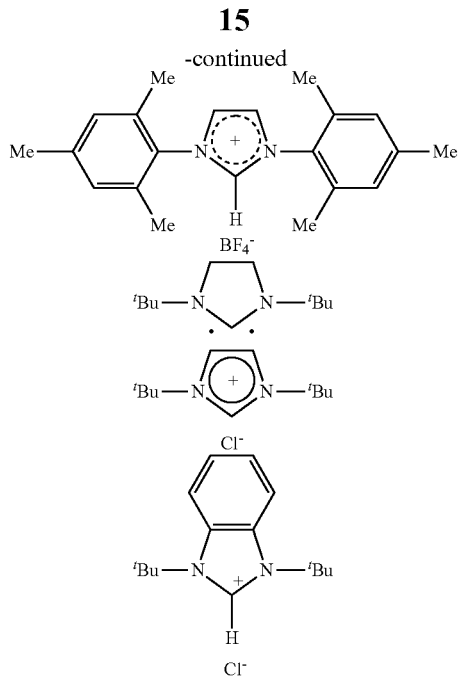

Illustrative and non-limiting examples of metalalactone complexes (representative nickelalactones) suitable for use as described herein include the following compounds (Cy=cyclohexyl, ᵗBu=tert-butyl):

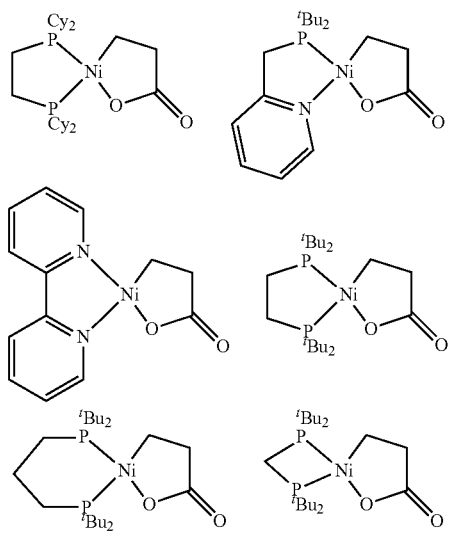

The transition metal precursor compounds corresponding to these illustrative metalalactones are shown below:

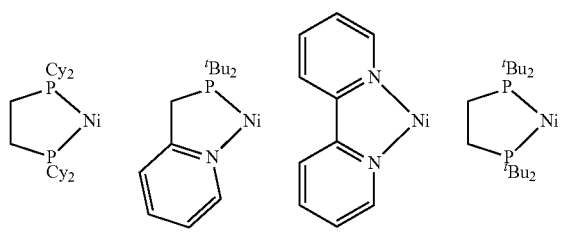

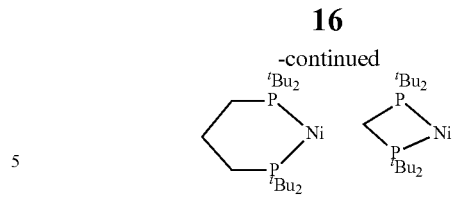

Metalalactones can be synthesized according to the following general reaction scheme (illustrated with nickel as the transition metal; $Ni(COD)_2$ is bis(1,5-cyclooctadiene)nickel(0)):

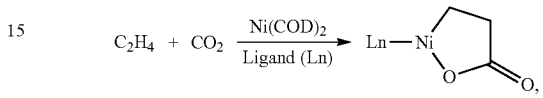

and according to suitable procedures well known to those of skill in the art.

Suitable ligands, transition metal precursor compounds, and metalalactones are not limited solely to those ligands, transition metal precursor compounds, and metalalactones disclosed herein. Other suitable ligands, transition metal precursor compounds, and metalalactones are described, for example, in U.S. Pat. Nos. 7,250,510, 8,642,803, and 8,697,909; Journal of Organometallic Chemistry, 1983, 251, C51-053; Z. Anorg. Allg. Chem., 1989, 577, 111-114; Journal of Organometallic Chemistry, 2004, 689, 2952-2962; Organometallics, 2004, Vol. 23, 5252-5259; Chem. Commun., 2006, 2510-2512; Organometallics, 2010, Vol. 29, 2199-2202; Chem. Eur. J., 2012, 18, 14017-14025; Organometallics, 2013, 32 (7), 2152-2159; and Chem. Eur. J., 2014, Vol. 20, 11, 3205-3211; the disclosures of which are incorporated herein by reference in their entirety.

Generally, the features of the processes disclosed herein (e.g., the metalalactone, the diluent, the anionic polyelectrolyte, the α,β-unsaturated carboxylic acid or salt thereof, the transition metal precursor compound, the olefin, and the conditions under which the α,β-unsaturated carboxylic acid, or a salt thereof, is formed, among others) are independently described, and these features can be combined in any combination to further describe the disclosed processes.

In accordance with an aspect of the present disclosure, a process for performing a metalalactone elimination reaction is disclosed, in which the process forms an α,β-unsaturated carboxylic acid or salt thereof. This process can comprise (or consist essentially of, or consist of):

(1) contacting
  (a) a metalalactone comprising at least one ligand;
  (b) a diluent; and
  (c) an anionic polyelectrolyte having associated metal cations to provide a reaction mixture; and
(2) applying conditions to the reaction mixture suitable to induce a metalalactone elimination reaction to produce the α,β-unsaturated carboxylic acid or a salt thereof.

Suitable metalalactones, diluents, and anionic polyelectrolytes are disclosed hereinabove. In this process for performing a metalalactone elimination reaction, for instance, at least a portion of the diluent can comprise the α,β-unsaturated carboxylic acid, or the salt thereof, that is formed in step (2) of this process.

In accordance with another aspect of the present disclosure, a process for producing an α,β-unsaturated carboxylic acid, or a salt thereof, is disclosed. This process can comprise (or consist essentially of, or consist of):

(1) contacting
  (a) a metalalactone comprising at least one ligand;
  (b) a diluent; and
  (c) an anionic polyelectrolyte having associated metal cations to provide a reaction mixture comprising an adduct of the metalalactone and the anionic polyelectrolyte and its associated metal cations; and
(2) applying conditions to the reaction mixture suitable to form the α,β-unsaturated carboxylic acid or a salt thereof.

In this process for producing an α,β-unsaturated carboxylic acid or a salt thereof, for instance, at least a portion of the diluent of the reaction mixture comprising the adduct of the metalalactone can be removed after step (1), and before step (2), of this process. Suitable metalalactones, diluents, and anionic polyelectrolytes are disclosed hereinabove.

As discussed further in this disclosure, the above processes can further comprise a step of contacting a transition metal precursor compound comprising at least one first ligand, an olefin, and carbon dioxide ($CO_2$) to form the metalalactone comprising at least one ligand. That is, at least one ligand of the transition metal precursor compound can be carried over to the metalalactone. In further aspects, the above processes can further comprise a step of contacting a transition metal precursor compound comprising at least one first ligand with at least one second ligand, an olefin, and carbon dioxide ($CO_2$) to form the metalalactone comprising at least one ligand. In this aspect, the ligand set of the metalalactone typically comprises the at least one second ligand. That is, the metalalactone ligand can comprise the at least one first ligand, the at least one second ligand, or a combination thereof.

In some aspects, the contacting step—step (1)—of the above processes can include contacting, in any order, the metalalactone, the diluent, and the anionic polyelectrolyte, and additional unrecited materials. In other aspects, the contacting step can consist essentially of, or consist of, the metalalactone, the diluent, and the anionic polyelectrolyte components Likewise, additional materials or features can be employed in the applying conditions step—step (2)—that forms or produces the α,β-unsaturated carboxylic acid, or the salt thereof. Further, it is contemplated that these processes for producing an α,β-unsaturated carboxylic acid or a salt thereof by a metalalactone elimination reaction can employ more than one metalalactone and/or more than one anionic polyelectrolyte. Additionally, a mixture or combination of two or more diluents can be employed.

Any suitable reactor, vessel, or container can be used to contact the metalalactone, diluent, and anionic polyelectrolyte, non-limiting examples of which can include a flow reactor, a continuous reactor, a fixed bed reactor, a moving reactor bed, and a stirred tank reactor, including more than one reactor in series or in parallel, and including any combination of reactor types and arrangements. In particular aspects consistent with this disclosure, the metalalactone and the diluent can contact a fixed bed of the anionic polyelectrolyte, for instance, in a suitable vessel, such as in a continuous fixed bed reactor. In further aspects, combinations of more than one anionic polyelectrolyte can be used, such as a mixed bed of a first anionic polyelectrolyte and a second anionic polyelectrolyte, or sequential beds of a first anionic polyelectrolyte and a second anionic polyelectrolyte. In these and other aspects, the feed stream can flow upward or downward through the fixed bed. For instance, the metalalactone and the diluent can contact the first anionic polyelectrolyte and then the second anionic polyelectrolyte in a downward flow orientation, and the reverse in an upward flow orientation. In a different aspect, the metalalactone and the anionic polyelectrolyte can be contacted by mixing or stirring in the diluent, for instance, in a suitable vessel, such as a stirred tank reactor.

Step (1) of the process for producing an α,β-unsaturated carboxylic acid or a salt thereof also recites forming an adduct of the metalalactone and the anionic polyelectrolyte and its associated metal cations. Without intending to be bound by theory, there is some interaction between the metalalactone and the anionic polyelectrolyte and its associated metal cations that are believed to destabilize the metalalactone for its elimination of the metal acrylate. This interaction can be referred to generally as an adduct of the metalalactone and the anionic polyelectrolyte or an adduct of the α,β-unsaturated carboxylic acid with the anionic polyelectrolyte. This adduct can contain all or a portion of the α,β-unsaturated carboxylic acid and can be inclusive of salts of the α,β-unsaturated carboxylic acid.

Accordingly, applying conditions to the reaction mixture suitable to form an α,β-unsaturated carboxylic acid or a salt thereof is intended to reflect any concomitant or subsequent conditions to step (1) of the above processes that release the α,β-unsaturated carboxylic acid or a salt thereof from the adduct, regardless of the specific nature of the adduct.

For example, in step (2) of the process of applying conditions to the reaction mixture suitable to form an α,β-unsaturated carboxylic acid or a salt thereof, the adduct of the metalalactone and the anionic polyelectrolyte and its associated metal cations as defined herein is subjected to some chemical or other conditions or treatment to produce the α,β-unsaturated carboxylic acid or its salt. Various methods can be used to liberate the α,β-unsaturated carboxylic acid or its salt, from the anionic polyelectrolyte. In one aspect, for instance, the treating step can comprise contacting the adduct of the metalalactone and the anionic polyelectrolyte and its associated metal cations with an acid. Representative and non-limiting examples of suitable acids can include HCl, acetic acid, and the like, as well as combinations thereof. In another aspect, the treating step can comprise contacting the adduct of the metalalactone and the anionic polyelectrolyte and its associated metal cations with a base. Representative and non-limiting examples of suitable bases can include carbonates (e.g., $Na_2CO_3$, $Cs_2CO_3$, $MgCO_3$), hydroxides (e.g., $Mg(OH)_2$, $Na(OH)$), alkoxides (e.g., $Al(O^iPr)_3$, $Na(O^tBu)$, $Mg(OEt)_2$), and the like, as well as combinations thereof ($^iPr$=isopropyl, $^tBu$=tert-butyl, Et=ethyl). In yet another aspect, the treating step can comprise contacting the adduct of the metalalactone and the anionic polyelectrolyte and its associated metal cations with a suitable solvent. Representative and non-limiting examples of suitable solvents can include carbonyl-containing solvents such as ketones, esters, amides, etc. (e.g., acetone, ethyl acetate, N,N-dimethylformamide, etc., as described herein above), alcohol solvents, water, and the like, as well as combinations thereof.

In still another aspect, the treating step can comprise heating the adduct of the metalalactone and the anionic polyelectrolyte and its associated metal cations to any suitable temperature. This temperature can be in a range, for example, from 50 to 1000° C., from 100 to 800° C., from 150 to 600° C., from 250 to 1000° C., from 250° C. to 550° C., or from 150° C. to 500° C. The duration of this heating step is not limited to any particular period of time, as long as the period of time is sufficient to liberate the α,β-unsaturated carboxylic acid from the anionic polyelectrolyte. As those of skill in the art recognize, the appropriate treating step depends upon several factors, such as the particular diluent used in the process, and the particular anionic polyelectrolyte used in the process, amongst other considerations. One further treatment step can comprise, for example, a workup step with additional olefin to displace an alkene-nickel bound acrylate.

In these processes for performing a metalalactone elimination reaction and for producing an α,β-unsaturated carboxylic acid (or a salt thereof), additional process steps can be conducted before, during, and/or after any of the steps described herein. As an example, these processes can further comprise a step (e.g., prior to step (1)) of contacting a transition metal precursor compound with an olefin and carbon dioxide to form the metalalactone. Transition metal precursor compound are described hereinabove. Illustrative and non-limiting examples of suitable olefins can include ethylene, propylene, butene (e.g., 1-butene), pentene, hexene (e.g., 1-hexene), heptane, octene (e.g., 1-octene), and styrene and the like, as well as combinations thereof.

Yet, in accordance with another aspect of the present disclosure, a process for producing an α,β-unsaturated carboxylic acid, or a salt thereof, is disclosed. This process can comprise (or consist essentially of, or consist of):

(1) contacting in any order
   (a) a transition metal precursor compound comprising at least one first ligand;
   (b) optionally, at least one second ligand;
   (c) an olefin;
   (d) carbon dioxide ($CO_2$);
   (e) a diluent; and
   (f) an anionic polyelectrolyte having associated metal cations to provide a reaction mixture; and
(2) applying conditions to the reaction mixture suitable to form an α,β-unsaturated carboxylic acid or a salt thereof.

In aspects of this process that utilizes a transition metal precursor compound comprising at least one first ligand, the olefin can be ethylene, and the step of contacting a transition metal precursor compound with an olefin and carbon dioxide ($CO_2$) can be conducted using any suitable pressure of ethylene, or any pressure of ethylene disclosed herein, e.g., from 10 psig (70 KPa) to 1,000 psig (6,895 KPa), from 25 psig (172 KPa) to 500 psig (3,447 KPa), or from 50 psig (345 KPa) to 300 psig (2,068 KPa), and the like. Further, the olefin can be ethylene, and the step of contacting a transition metal precursor compound with an olefin and carbon dioxide ($CO_2$) can be conducted using a constant addition of the olefin, a constant addition of carbon dioxide, or a constant addition of both the olefin and carbon dioxide, to provide the reaction mixture. By way of example, in a process wherein the ethylene and carbon dioxide ($CO_2$) are constantly added, the process can utilize an ethylene:$CO_2$ molar ratio of from 5:1 to 1:5, from 3:1 to 1:3, from 2:1 to 1:2, or about 1:1, to provide the reaction mixture.

According to a further aspect of the above process that utilizes a transition metal precursor compound, the process can include the step of contacting a transition metal precursor compound with an olefin and carbon dioxide ($CO_2$) conducted using any suitable pressure of $CO_2$, or any pressure of $CO_2$ disclosed herein, e.g., from 20 psig (138 KPa) to 2,000 psig (13,790 KPa), from 50 psig (345 KPa) to 750 psig (5,171 KPa), or from 100 psig (689 KPa) to 300 psig (2,068 KPa), and the like. In any of the processes disclosed herein, the processes can further comprise a step of monitoring the concentration of at least one reaction mixture component, at least one elimination reaction product, or a combination thereof, for any reason, such as to adjust process parameters in real time, to determine extent or reaction, or to stop the reaction at the desired point.

As illustrated, this process that utilizes a transition metal precursor compound comprising at least one first ligand includes one aspect in which no second ligand is employed in the contacting step, and another aspect in which a second ligand is used in the contacting step. That is, one aspect involves the contacting step of the process comprising contacting the transition metal precursor compound comprising at least one first ligand with the at least one second ligand. The order of contacting can be varied. For example, the contacting step of the process disclosed above can comprise contacting (a) the transition metal precursor compound comprising at least one first ligand with (b) the at least one second ligand to form a pre-contacted mixture, followed by contacting the pre-contacted mixture with the remaining components (c)-(f) in any order to provide the reaction mixture.

Further embodiments related to the order of contacting, for example, the contacting step can include or comprise contacting the metalalactone, the diluent, and the anionic polyelectrolyte in any order. The contacting step can also comprise contacting the metalalactone and the diluent to form a first mixture, followed by contacting the first mixture with the anionic polyelectrolyte to form the reaction mixture. In a further aspect, the contacting step can comprise contacting the diluent and the anionic polyelectrolyte to form a first mixture, followed by contacting the first mixture with the metalalactone to form the reaction mixture. In yet a further aspect, the contacting step of the process can further comprises contacting any number of additives, for example, additives that can be selected from an acid, a base, or a reductant.

Suitable transition metal-ligands, olefins, diluents, anionic polyelectrolytes with associated metal cations are disclosed hereinabove. In some aspects, the contacting step—step (1)—of this process can include contacting, in any order, the transition metal-ligand, the olefin, the diluent, the anionic polyelectrolyte and carbon dioxide, and additional unrecited materials. In other aspects, the contacting step can consist essentially of, or consist of, contacting, in any order, the transition metal-ligand, the olefin, the diluent, the anionic polyelectrolyte, and carbon dioxide. Likewise, additional materials or features can be employed in the forming step of step (2) of this process. Further, it is contemplated that this processes for producing an α,β-unsaturated carboxylic acid, or a salt thereof, can employ more than one transition metal-ligand complex and/or more than one anionic polyelectrolyte if desired and/or more than one olefin. Additionally, a mixture or combination of two or more diluents can be employed.

As above, any suitable reactor, vessel, or container can be used to contact the transition metal-ligand, olefin, diluent, anionic polyelectrolyte, and carbon dioxide, whether using a fixed bed of the anionic polyelectrolyte, a stirred tank for contacting (or mixing), or some other reactor configuration and process. While not wishing to be bound by the following theory, a proposed and illustrative reaction scheme for this process is provided below.

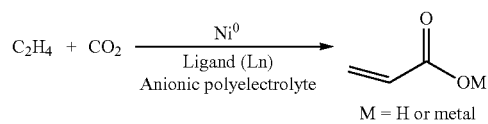

Independently, the contacting and forming steps of any of the processes disclosed herein (i.e., for performing a metalalactone elimination reaction, for producing an α,β-unsaturated carboxylic acid, or a salt thereof), can be conducted at a variety of temperatures, pressures, and time periods. For instance, the temperature at which the components in step (1) are initially contacted can be the same as, or different from, the temperature at which the forming step (2) is performed. As an illustrative example, in the contacting step, the components can be contacted initially at temperature T1 and, after this initial combining, the temperature can be increased to a temperature T2 for the forming step (e.g., to form the α,β-unsaturated carboxylic acid, or the salt thereof). Likewise, the pressure can be different in the contacting step and the forming step. Often, the time period in the contacting step can be referred to as the contact time, while the time period in forming step can be referred to as the reaction time. The contact time and the reaction time can be, and often are, different.

In an aspect, the contacting step and/or the forming step of the processes disclosed herein can be conducted at a temperature in a range from 0° C. to 250° C.; alternatively, from 20° C. to 200° C.; alternatively, from 0° C. to 95° C.; alternatively, from 10° C. to 75° C.; alternatively, from 10° C. to 50° C.; or alternatively, from 15° C. to 70° C. In these and other aspects, after the initial contacting, the temperature can be changed, if desired, to another temperature for the forming step. These temperature ranges also are meant to encompass circumstances where the contacting step and/or the forming step can be conducted at a series of different temperatures, instead of at a single fixed temperature, falling within the respective ranges.

In an aspect, the contacting step and/or the forming step of the processes disclosed herein can be conducted at a pressure in a range from 5 (34 KPa) to 10,000 psig (68,948 KPa), such as, for example, from 5 psig (34 KPa) to 2500 psig (17,237 KPa). In some aspects, the pressure can be in a range from 5 psig (34 KPa) to 500 psig (3,447 KPa); alternatively, from 25 psig (172 KPa) to 3000 psig (20,684 KPa); alternatively, from 45 psig (310 KPa) to 1000 psig (6,895 KPa); or alternatively, from 50 psig (345 KPa) to 250 psig (1,724 KPa).

The contacting step of the processes is not limited to any particular duration of time. That is, the respective components can be initially contacted rapidly, or over a longer period of time, before commencing the forming step. Hence, the contacting step can be conducted, for example, in a time period ranging from as little as 1-30 seconds to as long as 1-12 hours, or more. In non-continuous or batch operations, the appropriate reaction time for the forming step can depend upon, for example, the reaction temperature, the reaction pressure, and the ratios of the respective components in the contacting step, among other variables. Generally, however, the forming step can occur over a time period that can be in a range from 1 minute to 96 hours, such as, for example, from 2 minutes to 96 hours, from 5 minutes to 72 hours, from 10 minutes to 72 hours, or from 15 minutes to 48 hours.

If the process employed is a continuous process, then the metalalactone/anionic electrolyte catalyst contact/reaction time (or the transition metal-ligand/anionic electrolyte catalyst contact/reaction time) can be expressed in terms of weight hourly space velocity (WHSV)—the ratio of the weight of the metalalactone (or transition metal-ligand complex) which comes in contact with a given weight of anionic electrolyte per unit time (for example, $hr^{-1}$). While not limited thereto, the WHSV employed, based on the amount of the anionic electrolyte, can be in a range from 0.05 to 100 $hr^{-1}$, from 0.05 to 50 $hr^{-1}$, from 0.075 to 50 $hr^{-1}$, from 0.1 to 25 $hr^{-1}$, from 0.5 to 10 $hr^{-1}$, from 1 to 25 $hr^{-1}$, or from 1 to 5 $hr^{-1}$.

In the processes disclosed herein, the molar yield of the α,β-unsaturated carboxylic acid, or the salt thereof), based on the metalalactone (or the transition metal-ligand complex) is at least 2%, and more often can be at least 5%, at least 10%, or at least 15%. In particular aspects of this disclosure, the molar yield can be at least 18%, at least 20%, at least 25%, at least 35%, at least 50%, at least 60%, at least 75%, or at least 85%, or at least 90%, or at least 95%, or at least 100%. That is, catalytic formation of the α,β-unsaturated carboxylic acid or the salt thereof can be effected with the disclosed system. For example, the molar yield of the α,β-unsaturated carboxylic acid, or the salt thereof, based on the metalalactone or based on the transition metal precursor compound can be at least 20%, at least 40%, at least 60%, at least 80%, at least 100%, at least 120%, at least 140%, at least 160%, at least 180%, at least 200%, at least 250%, at least 300%, at least 350%, at least 400%, at least 450%, or at least 500%.

The specific α,β-unsaturated carboxylic acid (or salt thereof) that can be formed or produced using the processes of this disclosure is not particularly limited. Illustrative and non-limiting examples of the α,β-unsaturated carboxylic acid can include acrylic acid, methacrylic acid, 2-ethylacrylic acid, cinnamic acid, and the like, as well as combinations thereof. Illustrative and non-limiting examples of the salt of the α,β-unsaturated carboxylic acid can include sodium acrylate, potassium acrylate, magnesium acrylate, sodium (meth)acrylate, and the like, as well as combinations thereof.

Once formed, the α,β-unsaturated carboxylic acid (or salt thereof) can be purified and/or isolated and/or separated using suitable techniques which can include, but are not limited to, evaporation, distillation, chromatography, crystallization, extraction, washing, decanting, filtering, drying, and the like, including combinations of more than one of these techniques. In an aspect, the process can for performing a metalalactone elimination reaction (or the process for producing an α,β-unsaturated carboxylic acid, or a salt thereof) can further comprise a step of separating or isolating the α,β-unsaturated carboxylic acid (or salt thereof) from other components, e.g., the diluent, the anionic electrolyte, and the like.

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

General Considerations

Unless otherwise noted, all operations were performed under purified nitrogen or vacuum using standard Schlenk or glovebox techniques. Toluene (Honeywell) and tetrahydrofuran (Aldrich) was degassed and dried over activated 4 Å molecular sieves under nitrogen. Sodium tert-butoxide, potassium tert-butoxide, poly(4-vinylphenol) ($M_w$~11,000 g/mol), poly(4-vinylphenol-co-methyl(meth)acrylate) ($M_w$~8,000-12,000 g/mol), and brominated poly(4-vinylphenol) ($M_w$~5,800 g/mol) were purchased from Sigma- Aldrich and used as received. Phenol/formaldehyde resin was purchased as hollow beads (~5-127 μm) from Polysciences, Inc. Bis(1,5-cyclooctadiene)nickel(0) and 1,2-Bis(dicyclohexylphosphino)ethane were purchased from Strem and were used as received. (TMEDA)Ni(CH$_2$CH$_2$CO$_2$) was prepared according to literature procedures (Fischer, R; Nestler, B., and Schutz, H. Z. anorg. allg. Chem. 577 (1989) 111-114).

Preparation of Compounds

Sodium poly(4-vinylphenol). To sodium tert-butoxide (15 g, 125 mmol) and poly(4-vinylphenol) (12 g, 125 mmol) was added toluene (600 mL) in a 1 L round-bottomed flask equipped with a stirbar. The mixture was stirred for four days then frit filtered. The filter cake was washed with 30 mL of toluene followed by 15 mL of toluene, then allowed to dry. The dry cake was washed with 3×20 mL of toluene leaving a solid.

Potassium poly(4-vinylphenol). Prepared analogously to sodium poly(4-vinylphenol) substituting potassium tert-butoxide for sodium tert-butoxide.

Sodium poly(4-vinylphenol-co-methyl(meth)acrylate). Prepared analogously to sodium poly(4-vinylphenol) substituting poly(4-vinylphenol-co-methyl(meth)acrylate) for poly(4-vinylphenol).

Sodium poly(4-vinylphenol), brominated. Prepared analogously to sodium poly(4-vinylphenol) substituting poly(4-vinylphenol), brominated for poly(4-vinylphenol).

Sodium phenol/formaldehyde resin. Phenolic resin (phenol/formaldehyde resin) was suspended in a solution of sodium hydroxide in either water or methanol and stirred at 55° C. overnight prior to filtration, and subsequently washed with copious amounts of the solvent in which it was treated. The solid was then dried under vacuum prior to storage under nitrogen.

Examples 1-10

Experimental Procedure for Ethylene/Carbon Dioxide Coupling

The ethylene/carbon dioxide reaction of these examples is set out in reaction (1) below, and specific reagents, reaction conditions, and yields are set out in Table 1.

A 1-liter autoclave pressure reactor was charged with solvent followed by a combined mixture of Ni(COD)$_2$ (0.10 mmol), bis(dicyclohexylphosphino)ethane (0.11 mmol), and poly(4-vinylphenoxide) (1.00 g) in 10 mL of solvent. The reactor was set to 50° C., pressurized with ethylene at the desired level, and equilibrated for 5-10 minutes (min) prior to being pressurized and equilibrated with carbon dioxide. The reactor was then set to 100° C. and stirred for 6 hours. After this reaction time, and after cooling to ambient temperature, the reactor was slowly vented and the mixture was collected. The solvent was removed in vacuo and the residue was stirred in 10-20 mL of deuterium oxide for 30 min prior to the addition of a sorbic acid/acetone-d$_6$ solution. The mixture was filtered and analyzed by NMR (sorbic acid is used as the internal standard) for acrylate yield determination.

(1)

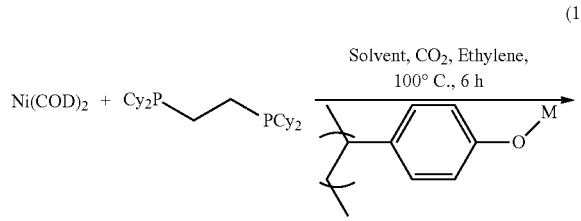

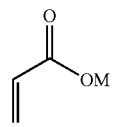

TABLE 1

Ethylene/carbon dioxide coupling and acrylate yields

| Example | M | Solvent | [Solvent] (mL) | [C$_2$H$_4$] (psi (KPa)) | [CO$_2$] (psi (KPa)) | Acrylate Yield (%) |
| --- | --- | --- | --- | --- | --- | --- |
| 1 | Na | Toluene | 300 | 150 (1,034) | 100 (689) | 14 |
| 2 | K | Toluene | 300 | 100 (689) | 150 (1,034) | 68 |
| 3 | K | Toluene | 300 | 150 (1,034) | 300 (2,068) | 117 |
| 4 | K | Toluene | 50 | 150 (1,034) | 300 (2,068) | 42 |
| 5 | K | Toluene | 50 | 75 (517) | 300 (2,068) | 25 |
| 6 | Na | Toluene | 300 | 150 (1,034) | 300 (2,068) | 104 |
| 7 | Na[A] | Toluene | 300 | 150 (1,034) | 300 (2,068) | 130 |
| 8 | Na | Toluene | 50 | 150 (1,034) | 300 (2,068) | 23 |
| 9 | Na | THF | 50 | 150 (1,034) | 300 (2,068) | 52 |
| 10 | Na | THF | 300 | 150 (1,034) | 300 (2,068) | 62 |

[A] 2.00 g of poly(4-vinylphenoxide) were used in this example.

Examples 11-17

Experimental Procedure for Nickelalactone Conversion to Acrylate

To study the elimination step of the disclosed process, the efficiencies of various alkoxides or aryloxides for the conversion of a diphosphine-stabilized nickelalactone to acrylic acid were assessed. Specifically, the following experiments show the efficiencies of sodium and potassium (4-vinylphenoxide) for the conversion of an in situ prepared diphosphine-stabilized nickelalactone, and the data were compared to the conversion using molecular sodium tert-butoxide for acrylate formation from the analogous nickelalactones. The metalalactone to acrylate conversion reaction of these examples is set out in reaction (2) below, and specific reagents, reaction conditions, and yields are set out in Table 2. In reaction (2), the "metal alkoxide" includes the polymeric alkoxides shown in Table 2.

In a 10 mL vial, (TMEDA)Ni(CH$_2$CH$_2$CO$_2$) (0.018 mmol), bis(dicyclohexylphosphino)-ethane (0.018 mmol), poly(4-vinylphenoxide), and solvent (5 mL) were combined and stirred at 60° C. for 30-60 min. Following removal of solvent, the solid residue was taken up in D$_2$O (3-5 mL) for 30 min and filtered. An aliquot of a prepared sorbic acid/acetone-d$_6$ solution was added for determination of acrylic acid yield by NMR.

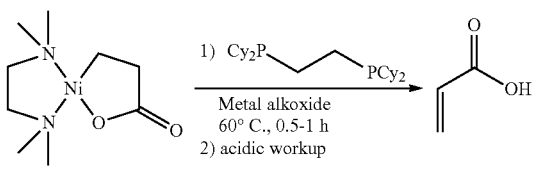

(2)

TABLE 2

Nickelalactone conversion to acrylate and acrylate yields

| Example | Metal Alkoxide | Solvent | [Metal Alkoxide] (mg) | % Yield |
|---|---|---|---|---|
| 11 | Sodium poly(4-vinylphenoxide) | Toluene | 100 | 33 |
| 12 | Sodium poly(4-vinylphenoxide) | Toluene | 250 | 32 |
| 13 | Sodium poly(4-vinylphenoxide) | Toluene | 25 | 15 |
| 14 | Potassium poly(4-vinylphenoxide) | Toluene | 100 | 24 |
| 15 | Sodium poly(4-vinylphenol-co-methyl(meth)acrylate) | Toluene | 100 | 66 |
| 16 | Sodium poly(4-vinylphenol), brominated | Toluene | 100 | 6 |
| 17 | Sodium tert-butoxide | THF | 7 | 16 |

The study from Table 2 reveals, among other things, that increasing the sodium poly(4-vinylphenoxide) amount from 100 mg to 250 mg (Examples 11 and 12) provides the same overall yield of the sodium acrylate/acrylic acid. Using the potassium salt (Example 14) as compared to the sodium salt (Example 11) of the poly(4-vinylphenoxide) somewhat lowered the yield of the sodium acrylate/acrylic acid.

Accordingly, this disclosure demonstrates at least the following: 1) a facile acid-base reaction that affords a metal polyvinylphenoxide or varients thereof in excellent yields with negligible byproducts; 2) a nickelalactone destabilization and cleavage that can proceed in surprisingly short time frames, that is, shorter times than expected (<1 hour); and 3) the increased loadings of metal polyvinylphenoxide does not diminish the resulting yield of the acrylate/acrylic acid.

Example 18

Polymeric Stationary Phases for Catalytic Acrylate Formation

The present disclosure also provides for using polymeric stationary phases, such as polyphenol resins (e.g. poly(4-vinylphenolate) resins) or polyaromatic resins (e.g. phenol-formaldehyde resins) in a column or other suitable solid state configuration, in which formation of the acrylate from a metalalactone (such as a nickelalactone) in a mobile phase can be effected.

FIG. 1 illustrates one way in which a polymeric stationary phase catalyst column can be configured, in which the coupling reaction and elution of the metal acrylate from the column can be carried out. As shown, a metal (e.g. sodium) poly(4-vinylphenolate) resins were found to be suitable anionic polyelectrolyte promoters or "co-catalysts" in the conversion of olefin/carbon dioxide-derived nickelalactone intermediates. This method can provide both easier separation of acrylate from other materials and ease of regeneration of the polymeric support materials to its salt form, such as sodium poly(4-vinylphenoxide).

Example 19-21

Sodium-Treated Crosslinked Polyaromatic Resins as Stoichiometric Co-Catalysts in Olefin/Carbon Dioxide Conversion to α,β-Unsaturated Carboxylates Because the metal (e.g. sodium) poly(4-vinylphenolate) resins were found to be suitable promoters and sources of cations in the conversion of olefin and carbon dioxide-derived nickelalactone intermediates, an evaluation of their crosslinked analogues was undertaken. It was believed that these crosslinked polyaromatic resins would be sufficiently insoluble in many commercial diluents to be applicability as a polymeric promoters and cation sources in a fixed bed/column reactor setting. This method further allows for the potential regeneration of the spent solid co-catalyst in both aqueous (for example, sodium hydroxide in water) and/or organic media (for example, sodium alkoxide in toluene).

The following reaction (3) illustrates the conversion reaction of an olefin and carbon dioxide-derived nickelalactone intermediate that was undertaken to evaluate some crosslinked polyelectrolyte analogues. Reaction conditions for reaction (3) are: 0.10 mmol [Ni], 0.11 mmol diphosphine ligand, 500 mL of toluene, 1.0 g of sodium-treated, crosslinked polyaromatic resin (solid activator). The reactor was equilibrated to 150 psi of ethylene followed by 300 psi of carbon dioxide prior to heating. The yield reported in Table 3 was determined by $^1$H NMR spectroscopy in a $D_2O/(CD_3)_2CO$ mixture relative to a sorbic acid standard.

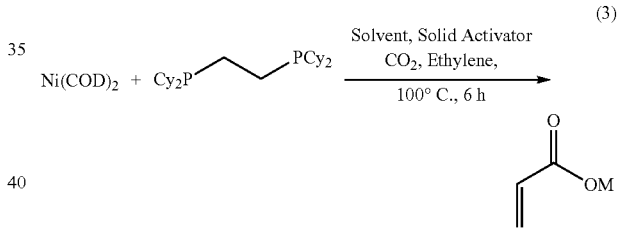

(3)

The following table describe various examples where commercial polyaromatic resins, which were either further treated with a sodium base under appropriate conditions or are commercially available in the sodium form, were found to be effective in the nickel-mediated synthesis of sodium acrylate from ethylene and carbon dioxide.

TABLE 3

Nickel-mediated conversion of carbon dioxide and ethylene to sodium acrylate with sodium treated polyaromatics.[A]

| Example | Solvent | Co-catalyst Solid | Base & Sodium Source | [Solid]:[Na] (wt) | Acrylate yield (%) |
|---|---|---|---|---|---|
| 19 | toluene | Phenol/Formaldehyde | NaOH (MeOH) | 0.3 | 1.8 |
| 20 | toluene | Phenol/Formaldehyde | NaOH (aq) | 0.3 | 6.0 |
| 21 | toluene | Phenol/Formaldehyde | NaO-t-Bu | 1.0 | n.d.[B] |

[A]Reaction Conditions: 0.10 mmol [Ni], 0.11 mmol diphosphine ligand, 500 mL toluene, 1.0 g solid activator (phenol-formaldehyde resin). Reactor was equilibrated to 150 psi ethylene followed by 300 psi carbon dioxide prior to heating. Yield determined by $^1$H NMR spectroscopy in $D_2O/(CD_3)_2CO$ mixture relative to sorbic acid standard.
[B]None detected.

Even though the yields of acrylate when employing these sodium-treated crosslinked resins may be modest, the data indicate that the nickel-mediated conversion of carbon dioxide and ethylene to sodium acrylate with sodium treated crosslinked polyaromatic resins can be carried out. Further, the insolubilities of these resins in many commercial solvents will allow for their utility in fixed bed/column configurations.

The phenol/formaldehyde resins can be treated with sodium hydroxide to produce what are believed to be sodium aryloxide sites that are active for promoting nickelalactone scission, and more so when the NaOH is dissolved in water to provide a higher solubility (Example 20) versus methanol (Example 19).

Example 22

Crosslinked Polyaromatic Resin Co-catalysts in Olefin/Carbon Dioxide Conversion to α,β-Unsaturated Carboxylates, using Co-monomers In this example, co-monomer phenol compounds are used together with formaldehyde to prepare the crosslinked polyaromatic resins for use as described according to the disclosure. The resin was prepared using the co-monomer combination of resorcinol (m-dihydroxybenzene) and 2-fluorophenol monomer with formaldehyde, and the resulting resin was sodium-treated (NaOH, dissolved in water or alcohol) to generate the anionic polyelectrolyte, according to equation (4).

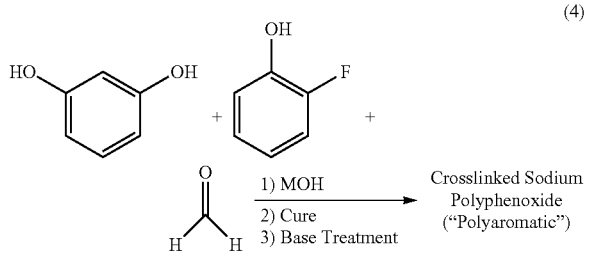

(4)

The polyaromatic resin is thought to act as a co-catalyst upon treatment with sodium hydroxide because of what are believed to be sodium aryloxide sites that promote nickelalactone scission. It is noted that increased crosslink density is obtained using longer drying times to remove trapped excess water.

Examples 23-26

Additional Stationary Phases for Catalytic Acrylate Formation

The present disclosure also provides for using other polymeric stationary phases and modifications thereof, for example, in a column or other suitable solid state configuration. Further variations of this technology include but are not limited to the following examples.

Example 23. Polymer modifications that include acid-base reaction being effected using a wide range of metal bases, including alkali and alkaline hydroxides, alkoxides, aryloxides, amides, alkyl or aryl amides, and the like, such that an assortment of electrophiles can be used in nickelalactone destabilization as demonstrated herein for the polyvinylphenols.

Example 24. Polymer modifications can also include using variants of the polyvinylphenol, that can be prepared by polymerization of hydroxyl-substituted styrenes having a variety of organic and inorganic substituents, such as alkyls, halogens, and heteroatom substituents.

Example 25. Polymer modifications can also include using co-polymers based on, for example, the co-polymerization of a protected hydroxyl-substituted styrene (such as acetoxystyrene) with other styrenes and (meth)acrylates (typically followed by hydrolysis to generate the polyvinylphenol co-polymer) to produce libraries of polymeric electrophiles.

Example 26. Polymer support variations are also envisioned, including for example polymers that can be supported onto beads or other surfaces. One class of polymer support variation that is envisioned is a cast polymer that can function as an ion exchange membrane.

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following embodiments. Many embodiments are described as "comprising" certain components or steps, but alternatively, can "consist essentially of" or "consist of" those components or steps unless specifically stated otherwise.

Embodiment 1. A process for forming an α,β-unsaturated carboxylic acid or salt thereof, the process comprising
   (1) contacting
      (a) a metalalactone comprising at least one ligand;
      (b) a diluent; and
      (c) an anionic polyelectrolyte having associated metal cations to provide a reaction mixture; and
   (2) applying conditions to the reaction mixture suitable to induce a metalalactone elimination reaction to produce the α,β-unsaturated carboxylic acid or a salt thereof.

Embodiment 2. A process for producing an α,β-unsaturated carboxylic acid or a salt thereof, the process comprising:
   (1) contacting
      (a) a metalalactone comprising at least one ligand;
      (b) a diluent; and
      (c) an anionic polyelectrolyte having associated metal cations to provide a reaction mixture comprising an adduct of the metalalactone and the anionic polyelectrolyte and its associated metal cations; and
   (2) applying conditions to the reaction mixture suitable to form the α,β-unsaturated carboxylic acid or a salt thereof.

Embodiment 3. A process for producing an α,β-unsaturated carboxylic acid or a salt thereof, the process comprising:
   (1) contacting in any order
      (a) a transition metal precursor compound comprising at least one first ligand;
      (b) optionally, at least one second ligand;
      (c) an olefin;
      (d) carbon dioxide ($CO_2$);
      (e) a diluent; and
      (f) an anionic polyelectrolyte having associated metal cations to provide a reaction mixture; and
   (2) applying conditions to the reaction mixture suitable to form the α,β-unsaturated carboxylic acid or a salt thereof.

Embodiment 4. The process according to any one of embodiments 1-3, wherein the anionic polyelectrolyte is insoluble in the diluent or the reaction mixture.

Embodiment 5. The process according to any one of embodiments 1-3, wherein the anionic polyelectrolyte is soluble in the diluent or the reaction mixture.

Embodiment 6. The process according to any one of embodiments 1-3, wherein the anionic polyelectrolyte comprises an alkoxide, an aryloxide, an acrylate, a (meth) acrylate, a sulfonate, an alkyl thiolate, an aryl thiolate, an alkyl amide, or an aryl amine groups.

Embodiment 7. The process according to any one of embodiments 1-3, wherein the anionic polyelectrolyte comprises a poly(vinyl aryloxide), a poly(vinyl alkoxide), a poly(acrylate), a poly((meth)acrylate), a poly(styrene sulfonate), a phenol-formaldehyde resin, a polyhydroxyarene-formaldehyde resin (such as a resorcinol-formaldehyde resin), a polyhydroxyarene- and fluorophenol-formaldehyde resin (such as a resorcinol- and 2-fluorophenol-formaldehyde resin), a poly(vinyl arylamide), a poly(vinyl alkylamide), or combinations thereof.

Embodiment 8. The process according to any one of embodiments 1-5, wherein the anionic polyelectrolyte comprises any suitable Lewis acidic metal cation or any Lewis acidic metal cation disclosed herein.

Embodiment 9. The process according to any one of embodiments 1-5, wherein the associated metal cations are an alkali metal, an alkaline earth metal, or a combination thereof.

Embodiment 10. The process according to any one of embodiments 1-5, wherein the associated metal cations are lithium, sodium, potassium, magnesium, calcium, strontium, barium, aluminum, or zinc.

Embodiment 11. The process according to any one of embodiments 1-5, wherein the associated metal cations are sodium or potassium.

Embodiment 12. The process according to any one of embodiments 1-3, wherein the anionic polyelectrolyte comprises a poly(vinyl aryloxide), a poly(vinyl alkoxide), a substituted analog thereof, or a combination thereof.

Embodiment 13. The process according to any one of embodiments 1-3, wherein the anionic polyelectrolyte comprises sodium(poly-4-vinylphenoxide).

Embodiment 14. The process according to any one of embodiments 1-3, wherein the anionic polyelectrolyte comprises a phenol-formaldehyde resin, a polyhydroxyarene-formaldehyde resin (such as a resorcinol-formaldehyde resin), a polyhydroxyarene- and fluorophenol-formaldehyde resin (such as a resorcinol- and 2-fluorophenol-formaldehyde resin), or combinations thereof.

Embodiment 15. The process according to any one of embodiments 1-3, wherein the anionic polyelectrolyte comprises a phenol-formaldehyde resin, a resorcinol-formaldehyde resin, a resorcinol- and fluorophenol-formaldehyde resin, or combinations thereof.

Embodiment 16. The process according to any one of embodiments 1-3, wherein the anionic polyelectrolyte comprises a phenol-formaldehyde resin or a resorcinol- and 2-fluorophenol-formaldehyde resin.

Embodiment 17. The process according to any one of embodiments 1-3, wherein the anionic polyelectrolyte comprises a phenol-formaldehyde resin.

Embodiment 18. The process according to any one of embodiments 1-17, wherein the diluent comprises any suitable non-protic solvent, or any non-protic solvent disclosed herein.

Embodiment 19. The process according to any one of embodiments 1-17, wherein the diluent comprises any suitable weakly coordinating or non-coordinating solvent, or any weakly coordinating or non-coordinating solvent disclosed herein.

Embodiment 20. The process according to any one of embodiments 1-17, wherein the diluent comprises any suitable aromatic hydrocarbon solvent, or any aromatic hydrocarbon solvent disclosed herein, e.g., benzene, xylene, toluene, etc.

Embodiment 21. The process according to any one of embodiments 1-17, wherein the diluent comprises any suitable ether solvent, or any ether solvent disclosed herein, e.g., THF, dimethyl ether, diethyl ether, dibutyl ether, etc.

Embodiment 22. The process according to any one of embodiments 1-17, wherein the diluent comprises any suitable carbonyl-containing solvent, or any carbonyl-containing solvent disclosed herein, e.g., ketones, esters, amides, etc. (e.g., acetone, ethyl acetate, N,N-dimethylformamide, etc.).

Embodiment 23. The process according to any one of embodiments 1-17, wherein the diluent comprises any suitable halogenated aromatic hydrocarbon solvent, or any halogenated aromatic hydrocarbon solvent disclosed herein, e.g., chlorobenzene, dichlorobenzene, etc.

Embodiment 24. The process according to any one of embodiments 1-17, wherein the diluent comprises THF, 2,5-Me$_2$THF, methanol, acetone, toluene, chlorobenzene, pyridine, or a combination thereof.

Embodiment 25. The process according to any one of the preceding embodiments, wherein the diluent comprises carbon dioxide.

Embodiment 26. The process according to any one of the preceding embodiments, wherein at least a portion of the diluent comprises the α,β-unsaturated carboxylic acid or the salt thereof, formed in the process.

Embodiment 27. The process according to any one of embodiments 3-26, wherein the contacting step further comprises contacting an additive selected from an acid, a base, or a reductant.

Embodiment 28. The process according to any one of embodiments 3-26, wherein the contacting step comprises contacting the transition metal precursor compound comprising at least one first ligand with the at least one second ligand.

Embodiment 29. The process according to any one of embodiments 3-26, wherein the contacting step comprises contacting (a) the transition metal precursor compound comprising at least one first ligand with (b) the at least one second ligand to form a pre-contacted mixture, followed by contacting the pre-contacted mixture with the remaining components (c)-(f) in any order to provide the reaction mixture.

Embodiment 30. The process according to any one of embodiments 1-2 and 4-26, wherein the contacting step comprises contacting the metalalactone, the diluent, and the anionic polyelectrolyte in any order.

Embodiment 31. The process according to any one of embodiments 1-2 and 4-26, wherein the contacting step comprises contacting the metalalactone and the diluent to form a first mixture, followed by contacting the first mixture with the anionic polyelectrolyte to form the reaction mixture.

Embodiment 32. The process according to any one of embodiments 1-2 and 4-26, wherein the contacting step comprises contacting the diluent and the anionic polyelectrolyte to form a first mixture, followed by contacting the first mixture with the metalalactone to form the reaction mixture.

Embodiment 33. The process according to any one of embodiments 1-26, wherein the conditions suitable to form the α,β-unsaturated carboxylic acid or a salt thereof comprise contacting the reaction mixture with any suitable acid, or any acid disclosed herein, e.g., HCl, acetic acid, etc.

Embodiment 34. The process according to any one of embodiments 1-26, wherein the conditions suitable to form the α,β-unsaturated carboxylic acid or a salt thereof comprise contacting the reaction mixture with any suitable solvent, or any solvent disclosed herein, e.g., carbonyl-containing solvents such as ketones, esters, amides, etc. (e.g., acetone, ethyl acetate, N,N-dimethylformamide), alcohols, water, etc.

Embodiment 35. The process according to any one of the preceding embodiments, wherein the conditions suitable to form the α,β-unsaturated carboxylic acid or a salt thereof comprise heating the reaction mixture to any suitable temperature, or a temperature in any range disclosed herein, e.g., from 50 to 1000° C., from 100 to 800° C., from 150 to 600° C., from 250 to 550° C., etc.

Embodiment 36. The process according to any one of the preceding embodiments, wherein the molar yield of the α,β-unsaturated carboxylic acid, or the salt thereof, based on the metalalactone (in those preceding embodiments comprising a metalalactone) or based on the transition metal precursor compound (in those preceding embodiments comprising a transition metal precursor compound) is in any range disclosed herein, e.g., at least 20%, at least 40%, at least 60%, at least 80%, at least 100%, at least 120%, at least 140%, at least 160%, at least 180%, at least 200%, at least 250%, at least 300%, at least 350%, at least 400%, at least 450%, or at least 500%, etc.

Embodiment 37. The process according to any one of the preceding embodiments, wherein the contacting step and/or the forming step is/are conducted at any suitable pressure or at any pressure disclosed herein, e.g., from 5 psig (34 KPa) to 10,000 psig (68,948 KPa), from 45 psig (310 KPa) to 1000 psig (6,895KPa), etc.

Embodiment 38. The process according to any one of the preceding embodiments, wherein the contacting step and/or the applying step is/are conducted at any suitable temperature or at any temperature disclosed herein, e.g., from 0° C. to 250° C., from 0° C. to 95° C., from 15° C. to 70° C., etc.

Embodiment 39. The process according to any one of the preceding embodiments, wherein the contacting step is conducted at any suitable weight hourly space velocity (WHSV) or any WHSV disclosed herein, e.g., from 0.05 to 50 $hr^{-1}$, from 1 to 25 $hr^{-1}$, from 1 to 5 $hr^{-1}$, etc., based on the amount of the anionic polyelectrolyte.

Embodiment 40. The process according to any one of the preceding embodiments, wherein the process further comprises a step of isolating the α,β-unsaturated carboxylic acid, or the salt thereof, e.g., using any suitable separation/purification procedure or any separation/purification procedure disclosed herein, e.g., evaporation, distillation, chromatography, etc.

Embodiment 41. The process according to any one of embodiments 1-40, wherein the anionic polyelectrolyte of the contacting step (1) comprises a fixed bed.

Embodiment 42. The process according to any one of embodiments 1-40, wherein the anionic polyelectrolyte of the contacting step (1) is supported onto beads or is used in the absence of a support.

Embodiment 43. The process according to any one of embodiments 1-40, wherein the contacting step (1) is carried out by mixing/stirring the anionic polyelectrolyte in the diluent.

Embodiment 44. The process according to any one of the preceding embodiments, wherein the α,β-unsaturated carboxylic acid or a salt thereof comprises any suitable α,β-unsaturated carboxylic acid, or any α,β-unsaturated carboxylic acid disclosed herein, or a salt thereof, e.g., acrylic acid, methacrylic acid, 2-ethylacrylic acid, cinnamic acid, sodium acrylate, potassium acrylate, magnesium acrylate, sodium (meth)acrylate, etc.

Embodiment 45. The process according to any one of embodiments 1-2 or 4-44, further comprising a step of contacting a transition metal precursor compound comprising at least one first ligand, an olefin, and carbon dioxide ($CO_2$) to form the metalalactone comprising at least one ligand.

Embodiment 46. The process according to any one of embodiments 1-2 or 4-44, further comprising a step of contacting a transition metal precursor compound comprising at least one first ligand, at least one second ligand, an olefin, and carbon dioxide ($CO_2$) to form the metalalactone comprising at least one ligand.

Embodiment 47. The process according to embodiment 46, wherein the metalalactone ligand comprises the at least one first ligand, the at least one second ligand, or a combination thereof.

Embodiment 48. The process according to embodiment 46, wherein the metalalactone ligand comprises the at least one second ligand.

Embodiment 49. The process according to any one of embodiments 3 or 45, wherein the olefin comprises any suitable olefin or any olefin disclosed herein, e.g. ethylene, propylene, butene (e.g., 1-butene), pentene, hexene (e.g., 1-hexene), heptane, octene (e.g., 1-octene), styrene, etc.

Embodiment 50. The process according to any one of embodiments 3 or 45-49, wherein the olefin is ethylene, and the step of contacting a transition metal precursor compound with an olefin and carbon dioxide ($CO_2$) is conducted using any suitable pressure of ethylene, or any pressure of ethylene disclosed herein, e.g., from 10 psig (69 KPa) to 1,000 psig (6895 KPa), from 25 psig (172 KPa) to 500 psig (3,447 KPa), or from 50 psig (345 KPa) to 300 psig (2,068 KPa), etc.

Embodiment 51. The process according to any one of embodiments 3 or 45-49, wherein the olefin is ethylene, and the step of contacting a transition metal precursor compound with an olefin and carbon dioxide ($CO_2$) is conducted using a constant addition of the olefin and carbon dioxide to provide the reaction mixture.

Embodiment 52. The process according to embodiment 51, wherein the ethylene and carbon dioxide ($CO_2$) are constantly added in an ethylene:$CO_2$ molar ratio of from 3:1 to 1:3, to provide the reaction mixture.

Embodiment 53. The process according to any one of embodiments 3 or 45-49, wherein the step of contacting a transition metal precursor compound with the olefin and carbon dioxide ($CO_2$) is conducted using any suitable pressure of $CO_2$, or any pressure of $CO_2$ disclosed herein, e.g., from 20 psig (138 KPa) to 2,000 psig (13,790 KPa), from 50 psig (345 KPa) to 750 psig (5,171 KPa), or from 100 psig (689 KPa) to 300 psig (2,068 KPa), etc.

Embodiment 54. The process according to any one of the preceding embodiments, further comprising a step of monitoring the concentration of at least one reaction mixture component, at least one elimination reaction product, or a combination thereof.

Embodiment 55. The process according to any one of embodiments 1-54, wherein the metal of the metalalactone or the metal of the transition metal precursor compound is a Group 8-11 transition metal.

Embodiment 56. The process according to any one of embodiments 1-54, wherein the metal of the metalalactone or the metal of the transition metal precursor compound is Fe, Co, Ni, Cu, Ru, Rh, Pd, Ag, Ir, Pt, or Au.

Embodiment 57. The process according to any one of embodiments 1-54, wherein the metal of the metalalactone or the metal of the transition metal precursor compound is Ni, Fe, or Rh.

Embodiment 58. The process according to any one of embodiments 1-54, wherein the metal of the metalalactone or the metal of the transition metal precursor compound is Ni.

Embodiment 59. The process according to any one of embodiments 1-2 or 4-44, wherein the metalalactone is a nickelalactone, e.g., any suitable nickelalactone or any nickelalactone disclosed herein.

Embodiment 60. The process according to any one of embodiments 1-54, wherein any of the metalalactone ligand, the first ligand, or the second ligand is any suitable neutral electron donor group and/or Lewis base, or any neutral electron donor group and/or Lewis base disclosed herein.

Embodiment 61. The process according to any one of embodiments 1-54, wherein any of the metalalactone ligand, the first ligand, or the second ligand is a bidentate ligand.

Embodiment 62. The process according to any one of embodiments 1-54, wherein any of the metalalactone ligand, the first ligand, or the second ligand comprises at least one of a nitrogen, phosphorus, sulfur, or oxygen heteroatom.

Embodiment 63 The process according to any one of embodiments 1-54, wherein any of the metalalactone ligand, the first ligand, or the second ligand comprises or is selected from a diphosphine ligand, a diamine ligand, a diene ligand, a diether ligand, or dithioether ligand.

Embodiment 64. The process according to any one of embodiments 1-63, further comprising the step of regenerating the anionic polyelectrolyte by contacting the anionic polyelectrolyte with a base comprising a metal cation following the formation of the α,β-unsaturated carboxylic acid or a salt thereof.

Embodiment 65. The process according to embodiment 64, further comprising a step of washing the anionic polyelectrolyte with a solvent or the diluent.

Embodiment 66. The process according to embodiment 64, wherein the base comprises a metal cation is any suitable base, or any base disclosed herein, e.g., carbonates (e.g., $Na_2CO_3$, $Cs_2CO_3$, $MgCO_3$), hydroxides (e.g., $Mg(OH)_2$, NaOH), alkoxides (e.g., $Al(O^iPr)_3$, $Na(O^tBu)$, $Mg(OEt)_2$), and the like.

Embodiment 67. The process according to embodiment 64, wherein the step of regenerating the anionic polyelectrolyte is carried out in the absence of an alkoxide, an aryloxide, an amide, an alkylamide, an arylamide, an amine, a hydride, a phosphazene, and/or substituted analogs thereof.

Embodiment 68. The process according to embodiment 64, wherein the step of regenerating the anionic polyelectrolyte is carried out in the absence of an alkoxide, an aryloxide, a hydride, and/or a phosphazene.

Embodiment 69. The process according to embodiment 64, wherein the step of regenerating the anionic polyelectrolyte is carried out in the absence of an aryloxide or a metal hydride.

Embodiment 70. The process according to embodiment 64, wherein the step of regenerating the anionic polyelectrolyte is carried out in the absence of a non-nucleophilic base.

Embodiment 71. The process according to embodiment 64, wherein the anionic polyelectrolyte is unsupported.

Embodiment 72. The process according to any one of embodiments 1-3, wherein the metalalactone, metalalactone ligand, transition metal precursor compound, first ligand, second ligand, anionic polyelectrolyte, or metal cation is any suitable metalalactone, metalalactone ligand, transition metal precursor compound, first ligand, second ligand, anionic polyelectrolyte, or metal cation or is any metalalactone, metalalactone ligand, transition metal precursor compound, first ligand, second ligand, anionic polyelectrolyte, or metal cation disclosed herein.

Embodiment 73. A process for forming an α,β-unsaturated carboxylic acid or salt thereof, the process comprising:
(1) contacting
  (a) a metalalactone comprising a Group 8-10 metal and at least one ligand;
  (b) a diluent; and
  (c) a polyaromatic resin with associated metal cations to provide a reaction mixture; and
(2) applying conditions to the reaction mixture suitable to induce a metalalactone elimination reaction to form the α,β-unsaturated carboxylic acid or a salt thereof.

Embodiment 74. A for producing an α,β-unsaturated carboxylic acid or a salt thereof, the process comprising:
(1) contacting in any order
  (a) a group 8-11 transition metal precursor;
  (b) an olefin;
  (c) carbon dioxide ($CO_2$);
  (d) a diluent; and
  (e) a polyaromatic resin with associated metal cations to provide a reaction mixture; and
(2) applying conditions to the reaction mixture suitable to produce the α,β-unsaturated carboxylic acid or a salt thereof.

Embodiment 75. A process for producing an α,β-unsaturated carboxylic acid or a salt thereof, the process comprising:
(1) contacting in any order
  (a) a group 8-11 transition metal catalyst;
  (b) an olefin;
  (c) carbon dioxide ($CO_2$);
  (d) a diluent; and
  (e) an anionic polyelectrolyte with associated metal cations to provide a reaction mixture; and
(2) contacting the reaction mixture with a metal-containing base selected from an alkali metal or an alkaline earth metal oxide, hydroxide, alkoxide, aryloxide, amide, alkyl amide, arylamide, or carbonate to produce an α,β-unsaturated carboxylic acid salt;
wherein the contacting step is carried out in the absence of a non-nucleophilic base.

We claim:

1. A process for producing an α,β-unsaturated carboxylic acid or a salt thereof, the process comprising:
  a) contacting in any order
    (i) a group 8-11 transition metal precursor compound comprising at least one first ligand;
    (ii) at least one second ligand;
    (iii) an olefin;
    (iv) carbon dioxide ($CO_2$);
    (v) a diluent; and
    (vi) an anionic polyaromatic resin with associated metal cations to provide a reaction mixture; and b) applying conditions to the reaction mixture which produce the α,β-unsaturated carboxylic acid or a salt thereof.

2. The process according to claim 1, wherein the anionic polyaromatic resin with associated metal cations comprises a metallated phenol-formaldehyde resin, a metallated polyhydroxyarene-formaldehyde resin, or a metallated polyhydroxyarene- and fluorophenol-formaldehyde resin.

3. The process according to claim 1, wherein the anionic polyaromatic resin with associated metal cations comprises a sodium phenol-formaldehyde resin, a potassium phenol-formaldehyde resin, a sodium resorcinol- and 2-fluorophenol-formaldehyde resin, or a potassium resorcinol- and 2-fluorophenol-formaldehyde resin.

4. The process according to claim 1, wherein the anionic polyaromatic resin with associated metal cations is insoluble in the diluent or the reaction mixture.

5. The process according to claim 1, wherein:
a) the first ligand, the second ligand, or both the first ligand and the second ligand is a bidentate ligand; or
b) the first ligand, the second ligand, or both the first ligand and the second ligand comprise(s) at least one of a nitrogen, phosphorus, sulfur, or oxygen coordinating atom.

6. The process according to claim 1, wherein the first ligand, the second ligand, or both the first ligand and the second ligand comprise(s) a diphosphine ligand, a diamine ligand, a diene ligand, a diether ligand, or dithioether ligand.

7. The process according to claim 1, wherein the first ligand, the second ligand, or both the first ligand and the second ligand comprise(s) an ether ligand, an organic carbonyl ligand, a thioether ligand, an amine ligand, a nitrile ligand, a phosphine ligand, a diene ligand, or a carbene ligand.

8. The process according to claim 1, wherein the first ligand is a diene ligand and the second ligand is a diphosphine ligand.

9. The process according to claim 1, wherein the first ligand is 1,5-cyclooctadiene or TMEDA, and the second ligand is 1,2-bis(dicyclohexylphosphino)ethane or TMEDA.

10. The process according to claim 1, wherein the first ligand or the second ligand is selected from trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, tricyclohexylphosphine, trimethyl phosphite, triethyl phosphite, tripropyl phosphite, triisopropyl phosphite, tributyl phosphite and tricyclohexyl phosphite, 2-(di-t-butylphosphino)biphenyl, 2-di-t-butylphosphino-1,1'-binaphthyl, 2-(di-t-butylphosphino)-3,6-dimethoxy-2',4',6'-tri-i-propyl-1,1'-biphenyl, 2-di-t-butylphosphino-2'-methylbiphenyl, 2-(di-t-butylphosphinomethyl)pyridine, 2-di-t-butylphosphino-2',4',6'-tri-i-propyl-1,1'-biphenyl, 2-(dicyclohexylphosphino)biphenyl, (S)-(+)-(3,5-dioxa-4-phospha-cyclohepta[2,1-a;3,4-a']dinaphthalen-4-yl)dimethylamine, 2-(diphenylphosphino)-2'-methoxy -1,1'-binaphthyl, 1,2,3,4,5-pentaphenyl-1'-(di-t-butylphosphino) ferrocene, 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)-ethane, 1,2-bis(diisopropylphosphino)ethane, 1,2-bis(dibutyl-phosphino)ethane, 1,2-bis(di-t-butyl-phosphino)ethane, 1,2-bis (dicyclohexylphosphino)ethane, 1,3-bis(dicyclohexylphosphino)propane, 1,3-bis(diisopropylphosphino)propane, 1,3-bis(diphenylphosphino)propane, 1,3-bis(di-t-butylphosphino)propane, 1,4-bis(diisopropylphosphino) butane, 1,4-bis(diphenylphosphino)butane, 2,2'-bis[bis(3,5-dimethylphenyl)phosphino]-4,4',6,6'-tetramethoxybiphenyl, 2,6-bis(di-t-butylphosphinomethyl)pyridine, 2,2'-bis(dicyclohexylphosphino)-1,1'-biphenyl, bis(2-dicyclohexylphosphinophenyl)ether, 5,5'-bis(diphenylphosphino)-4,4'-bi-1,3-benzodioxole, 2-t-butylphosphinomethylpyridine, bis (diphenylphosphino)ferrocene, bis(diphenylphosphino) methane, bis(dicyclohexylphosphino)methane, bis(di-t-butylphosphino)methane, or TMEDA.

11. The process according to claim 1, wherein the first ligand or the second ligand is selected from

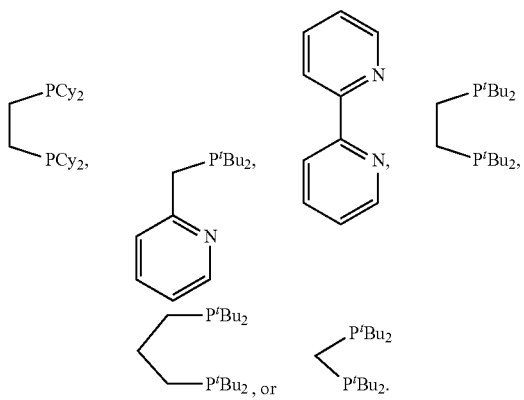

12. The process according to claim 1, wherein the contacting step comprises contacting (i) the group 8-11 transition metal precursor compound comprising at least one first ligand with (ii) the at least one second ligand to form a pre-contacted mixture, followed by contacting the pre-contacted mixture with the remaining components (iii)-(vi) in any order to provide the reaction mixture.

13. The process according to claim 1, wherein the reaction mixture comprises a metalalactone compound, the metalalactone compound comprising a group 8-11 transition metal metalalactone moiety and a) at least one first ligand or b) at least one second ligand.

14. The process according to claim 1, wherein the reaction mixture comprises an adduct of a metalalactone compound and the anionic polyaromatic resin with associated metal cations.

15. The process according to claim 1, wherein the associated metal cations are selected from a Group 1, 2, 12, or 13 metal cation.

16. The process according to claim 1, wherein the associated metal cations are lithium, sodium, potassium, magnesium, calcium, zinc or aluminum cations.

17. The process according to claim 1, wherein the conditions which produce the α,β-unsaturated carboxylic acid or a salt thereof comprise contacting the reaction mixture with a metal-containing base thereby producing a salt of the α,β-unsaturated carboxylic acid.

18. The process according to claim 17, wherein the metal-containing base is selected from an alkali metal or an alkaline earth metal oxide, hydroxide, alkoxide, aryloxide, amide, alkyl amide, arylamide, or carbonate.

19. The process according to claim 17, wherein the metal-containing base comprises $Na_2CO_3$, $Cs_2CO_3$, $MgCO_3$, NaOH, KOH, $Mg(OH)_2$, $Ca(OH)_2$, $Al(O^iPr)_3$, $Na(O^tBu)$, or $Mg(OEt)_2$.

20. The process according to claim 1, wherein the conditions which produce the α,β-unsaturated carboxylic acid or a salt thereof comprise at least one of the following conditions or any combination of the following conditions:
a) contacting the reaction mixture with a ketone, an ester, an amide, an alcohol, or water;
b) heating the reaction mixture to a temperature from 50 to 1000° C.;
c) conducting the contacting step at a total pressure of from 5 psig (34 KPa) to 10,000 psig (68,948 KPa);
d) conducting the contacting step at a temperature of from 0° C. to 250° C.; and/or
e) conducting the contacting step at a weight hourly space velocity (WHSV) of from 0.05 to 50 hr$^{-1}$, based on the amount of the anionic polyaromatic resin with associated metal cations.

21. The process according to claim 1, wherein the conditions which produce the α,β-unsaturated carboxylic acid or a salt thereof further produce a polyaromatic resin.

22. The process according to claim 21, further comprising the step of:
c) regenerating the anionic polyaromatic resin with associated metal cations by contacting the polyaromatic resin with a metal-containing base following the formation of the α,β-unsaturated carboxylic acid or the salt thereof.

23. The process according to claim 1, wherein a molar yield of the α,β-unsaturated carboxylic acid or a salt thereof based on the transition metal precursor compound is at least 100%.

24. The process according to claim 1, wherein the group 8-11 transition metal precursor compound comprises Ni.

25. The process according to claim 1, wherein the olefin comprises ethylene, propylene, butene, pentene, hexene, heptene, octene, or styrene.

26. The process according to claim 1, wherein:
a) the olefin is ethylene;
b) the diluent comprises a non-protic solvent, a weakly coordinating solvent, or a non-coordinating solvent; and
c) the step of contacting the group 8-11 transition metal precursor compound with the olefin and carbon dioxide is conducted by:
i) using from 10 psig (689 KPa) to 1,000 psig (6,902 KPa) of ethylene partial pressure, using a constant addition of the ethylene and carbon dioxide to provide the reaction mixture; or
ii) adding the ethylene and carbon dioxide in a constant or a variable ethylene:CO$_2$ molar ratio of from 10:1 to 1:10, to provide the reaction mixture.

27. The process according to claim 1, wherein the diluent comprises an aromatic hydrocarbon solvent, an ether solvent, a carbonyl-containing solvent, a halogenated aromatic hydrocarbon solvent, or combinations thereof.

28. A process for producing an α,β-unsaturated carboxylic acid or a salt thereof, the process comprising:
a) contacting in any order
(i) a metalalactone compound comprising a group 8-11 transition metal metalalactone moiety and at least one ligand in addition to the metalalactone moiety;
(ii) a diluent; and
(iii) an anionic polyaromatic resin with associated metal cations to provide a reaction mixture; and
b) applying conditions to the reaction mixture which induce a metalalactone elimination reaction to form the α,β-unsaturated carboxylic acid or a salt thereof.

29. A process for producing an α,β-unsaturated carboxylic acid or a salt thereof, the process comprising:
a) contacting in any order
(i) a group 8-11 transition metal precursor compound comprising at least one first ligand selected from a diene ligand, an ether ligand, an organic carbonyl ligand, a thioether ligand, an amine ligand, a nitrile ligand, a phosphine ligand, or a carbene ligand;
(ii) at least one second ligand selected from a from a diene ligand, an ether ligand, an organic carbonyl ligand, a thioether ligand, an amine ligand, a nitrile ligand, a phosphine ligand, or a carbene ligand;
(iii) an olefin;
(iv) carbon dioxide (CO$_2$);
(v) a diluent; and
(vi) an anionic polyaromatic resin with associated metal cations to provide a reaction mixture; and
(2) contacting the reaction mixture with a metal-containing base selected from an alkali metal or an alkaline earth metal oxide, hydroxide, alkoxide, aryloxide, amide, alkyl amide, arylamide, or carbonate to produce an α,β-unsaturated carboxylic acid salt;
wherein the contacting step is carried out in the absence of sodium hydride.

30. The process according to claim 22, wherein the regenerating step is carried out in the absence of an alkali metal hydride.

31. The process according to claim 17, wherein the contacting step is carried out in the absence of sodium hydride.

32. The process according to claim 28, wherein the anionic polyaromatic resin with associated metal cations comprises a metallated phenol-formaldehyde resin, a metallated polyhydroxyarene-formaldehyde resin, or a metallated polyhydroxyarene- and fluorophenol-formaldehyde resin.

33. The process according to claim 28, wherein the anionic polyaromatic resin with associated metal cations comprises a sodium phenol-formaldehyde resin, a potassium phenol-formaldehyde resin, a sodium resorcinol- and 2-fluorophenol-formaldehyde resin, or a potassium resorcinol- and 2-fluorophenol-formaldehyde resin.

\* \* \* \* \*